(12) United States Patent
Uenodan et al.

(10) Patent No.: US 11,353,350 B2
(45) Date of Patent: Jun. 7, 2022

(54) PHYSICAL QUANTITY DETECTION DEVICE

(71) Applicant: HITACHI AUTOMOTIVE SYSTEMS, LTD., Hitachinaka (JP)

(72) Inventors: Akira Uenodan, Hitachinaka (JP); Takahiro Miki, Hitachinaka (JP); Takayuki Yogo, Hitachinaka (JP); Binti Haridan Fatin Farhanah, Hitachinaka (JP); Tsutomu Kono, Hitachinaka (JP); Shinobu Tashiro, Hitachinaka (JP)

(73) Assignee: HITACHI ASTEMO, LTD., Ibaraki (JP)

(*) Notice: Subject to any disclaimer, the term of this patent is extended or adjusted under 35 U.S.C. 154(b) by 237 days.

(21) Appl. No.: 16/633,636

(22) PCT Filed: Aug. 6, 2018

(86) PCT No.: PCT/JP2018/029347
§ 371 (c)(1),
(2) Date: Jan. 24, 2020

(87) PCT Pub. No.: WO2019/064933
PCT Pub. Date: Apr. 4, 2019

(65) Prior Publication Data
US 2020/0209034 A1   Jul. 2, 2020

(30) Foreign Application Priority Data
Sep. 29, 2017   (JP) .............................. JP2017-192236

(51) Int. Cl.
*G01F 5/00* (2006.01)
*F02D 41/18* (2006.01)
(Continued)

(52) U.S. Cl.
CPC ............... *G01F 5/00* (2013.01); *G01K 13/02* (2013.01); *G01L 9/0055* (2013.01);
(Continued)

(58) Field of Classification Search
CPC .......... G01F 5/00; G01F 1/6842; G01F 15/04; G01N 33/0036; G01N 33/0037;
(Continued)

(56) References Cited

U.S. PATENT DOCUMENTS

2003/0094041 A1* 5/2003 Iwaki .................... G01F 1/6842
73/204.21
2005/0284216 A1* 12/2005 Tanaka .................... G01F 1/692
73/204.26

(Continued)

FOREIGN PATENT DOCUMENTS

| EP | 2029976 A1 | 3/2009 |
|---|---|---|
| JP | 2003-176740 A | 6/2003 |

(Continued)

*Primary Examiner* — Herbert K Roberts
(74) *Attorney, Agent, or Firm* — Volpe Koenig

(57) ABSTRACT

To obtain a low-pressure-loss physical quantity detection device that can detect a plurality of physical quantities of intake air. A physical quantity detection device of the present invention that detects a plurality of physical quantities of a measured gas flowing in a main passage, the physical quantity detection device includes: a circuit board on which a sensor that detects the plurality of physical quantities and an electronic component that controls the physical quantities are mountable; a circuit board accommodating unit that accommodates the circuit board; and a sub-passage in which a flow sensor is disposed. The circuit board is accommodated in the circuit board accommodating unit on an upstream side of the sub-passage, and disposed in parallel with the measured gas flowing through the main passage.

11 Claims, 33 Drawing Sheets

(51) Int. Cl.
  *G01F 15/04* (2006.01)
  *G01K 13/02* (2021.01)
  *G01L 9/00* (2006.01)
  *G01N 33/00* (2006.01)
  *G01K 13/024* (2021.01)

(52) U.S. Cl.
  CPC ....... *G01N 33/0036* (2013.01); *G01K 13/024* (2021.01); *G01K 2205/02* (2013.01)

(58) Field of Classification Search
  CPC  G01K 2205/02; G01K 2205/04; F02D 41/18; F02D 41/187; F02D 2200/0418; F02D 2200/0406; F02D 2200/0414
  See application file for complete search history.

(56)  References Cited

U.S. PATENT DOCUMENTS

| | | | | |
|---|---|---|---|---|
| 2015/0114098 | A1* | 4/2015 | Kamiya | G01F 15/043 73/114.34 |
| 2015/0177043 | A1* | 6/2015 | Tokuyasu | G01F 5/00 73/202.5 |
| 2016/0313227 | A1* | 10/2016 | Schneider | G01F 1/696 |

FOREIGN PATENT DOCUMENTS

| | | | | |
|---|---|---|---|---|
| JP | 2010-002329 | A | 1/2010 | |
| JP | 4968267 | B2 | 7/2012 | |
| JP | 2013-120103 | A | 6/2013 | |
| WO | 2007/137978 | A1 | 12/2007 | |
| WO | WO-2016017300 | A1 * | 2/2016 | ............. G01F 1/684 |

* cited by examiner

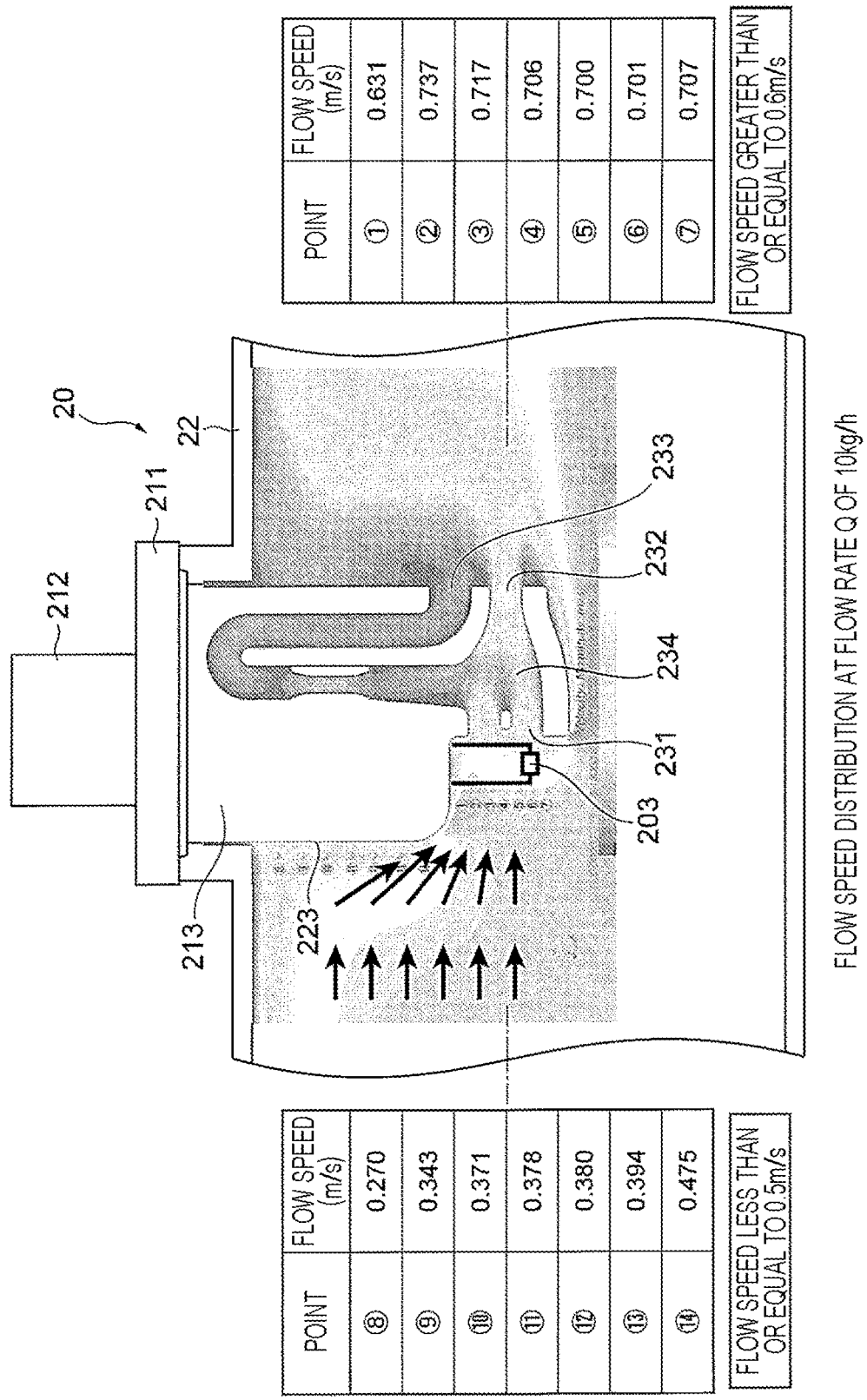

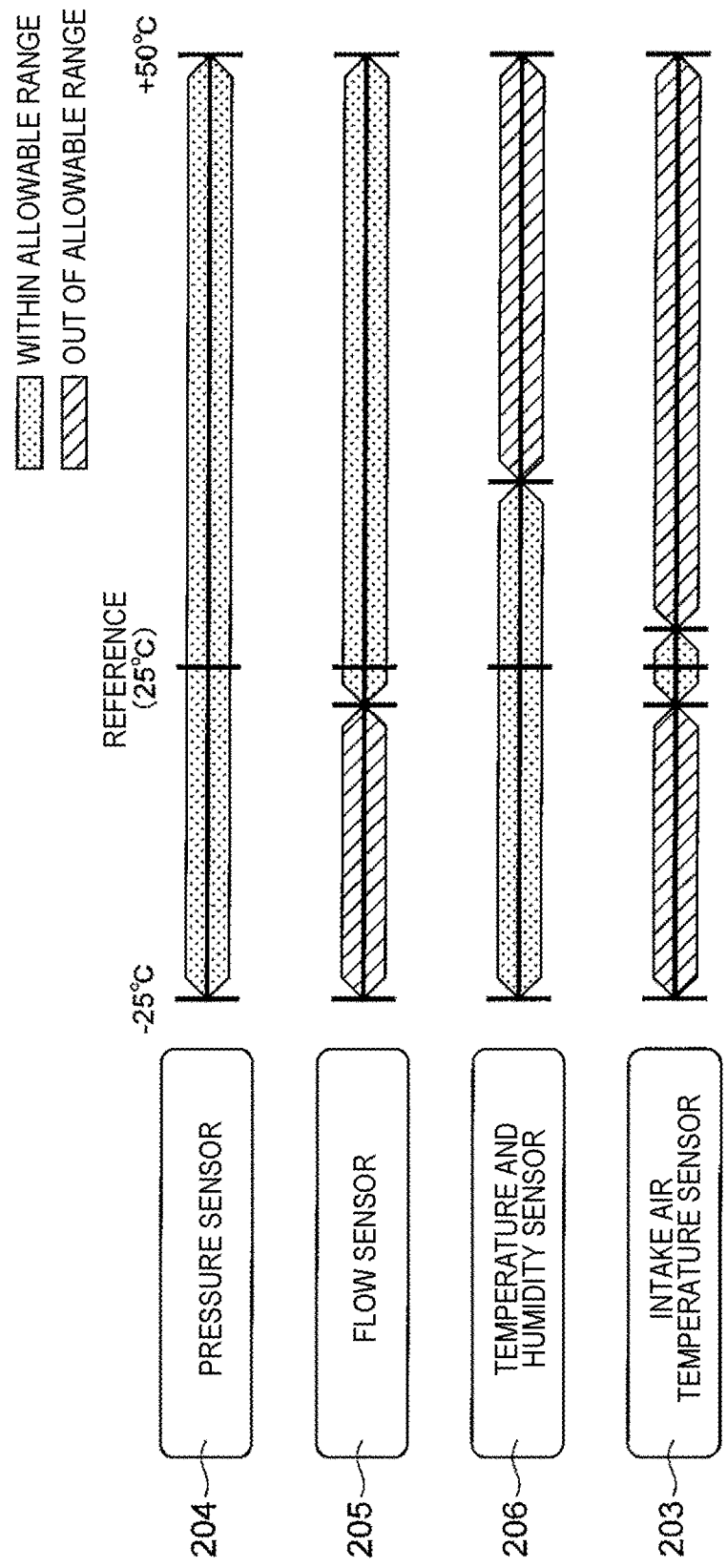

PHYSICAL QUANTITY DETECTION DEVICE

TECHNICAL FIELD

The present invention relates to a physical quantity detection device that detects a physical quantity of intake air of an internal combustion engine, for example.

BACKGROUND ART

For example, in a configuration of a thermal type flowmeter disclosed in PTL 1, a measuring unit protrudes from an inner wall of an intake passage toward a center of a passage, a sub-passage in which a flow is taken is disposed in the measuring unit, and a circuit board is disposed so as to straddle the bent sub-passage. The above conventional device proposes a low-pressure-loss physical quantity detection device in which the circuit board is efficiently disposed in the sub-passage to reduce a size in a longitudinal direction of the measuring unit.

For example, in a configuration of a thermal type flowmeter disclosed in PTL 2, the measuring unit protrudes from the inner wall of the intake passage toward the center of the passage, the circuit board is disposed on an upstream side of the measuring unit so as to be perpendicular to a flow of a main passage, and the sub-passage is disposed on a downstream side of the measuring unit. The above conventional device proposes a low-pressure-loss physical quantity detection device in which the circuit board and the sub-passage are disposed in parallel with the measuring unit to reduce the size in the longitudinal direction of the measuring unit.

CITATION LIST

Patent Literature

PTL 1: Japanese Patent No. 4968267
PTL 2: EP 2029976 A1

SUMMARY OF INVENTION

Technical Problem

A mounting method for being able to reduce a height by efficiently disposing the circuit board and the sub-passage is proposed in the above conventional device. For example, when the detection functions of an intake air temperature sensor, a humidity sensor, a pressure sensor, and the like are made multifunctional, the size of the circuit board is enlarged due to the increase in the numbers of control circuits, protection circuits, and circuit wires and addition of an electronic component, which results in an influence on size maintenance of the measuring unit.

In the configuration described in PTL 1, the pressure loss in the sub-passage increases by an increase in the number of circuit boards, which results in degradation of flow speed sensitivity of the flow sensor. When various sensors are installed in the circuit board, the various sensors become an obstacle, and there is a risk that noise performance and a pulsation characteristic of the flow sensor are degraded due to turbulence of a fluid.

In the configuration described in PTL 2, although the size in the longitudinal direction of the measuring unit can be maintained, the size in the thickness direction of the measuring unit is enlarged due to the increase in the number of circuit boards, which results in an increase in pressure.

The present invention has been made in view of the above points, and an object of the present invention is to provide a low-pressure-loss physical quantity detection device that can detect a plurality of physical quantities of intake air.

Solution to Problem

According to one aspect of the present invention, a physical quantity detection device that detects a plurality of physical quantities of a measured gas flowing in a main passage, the physical quantity detection device includes: a circuit board on which a sensor that detects the plurality of physical quantities and an electronic component that controls the physical quantities can be mounted; a circuit board accommodating unit accommodating the circuit board; and a sub-passage in which a flow sensor is disposed. The circuit board is accommodated in the circuit board accommodating unit on an upstream side of the sub-passage, and disposed in parallel with the measured gas flowing through the main passage.

Advantageous Effects of Invention

In the present invention, the sizes in the longitudinal direction and the thickness direction can be maintained and reduced, and a multifunction can be achieved while performance is ensured. Thus, the present invention is to provide a low-pressure-loss physical quantity detection device that can detect a plurality of physical quantities of intake air.

Further features associated with the present invention will become apparent from the description of the present description and the accompanying drawings. Problems, configurations, and effects other than those described above will be clarified by the following description of embodiments.

BRIEF DESCRIPTION OF DRAWINGS

FIG. 3 is a view illustrating a result of measuring a flow speed of a measured gas around the physical quantity detection device.

FIG. 7A is a numerical graph illustrating an allowable temperature error of each sensor.

DESCRIPTION OF EMBODIMENTS

Figure 1:
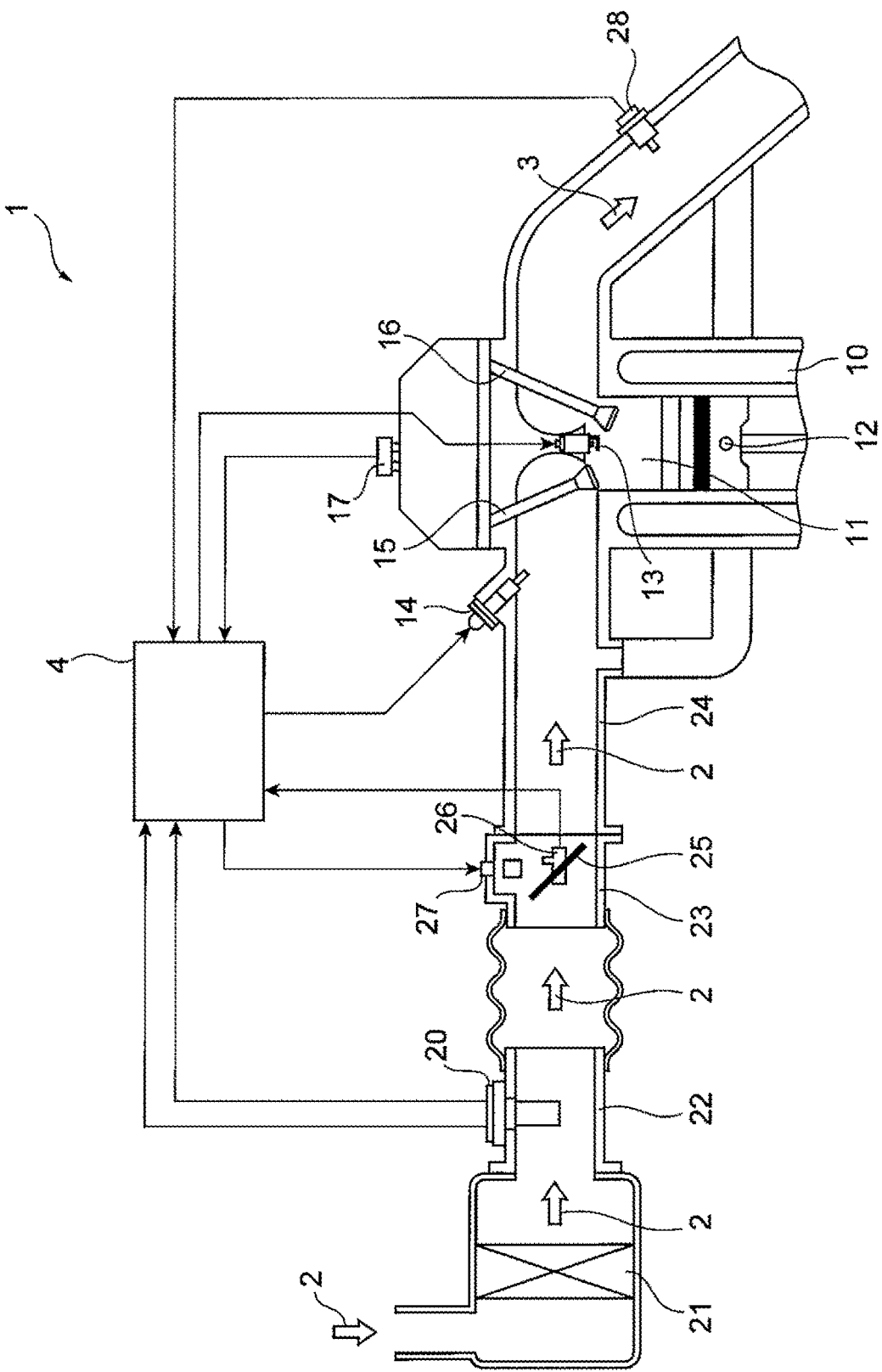
FIG. 1 is a system diagram illustrating an embodiment in which a physical quantity detection device according to the present invention is used in an internal combustion engine control system.

A mode for carrying out the invention (hereinafter referred to as an embodiment) described below solves various problems required as an actual product, solves various problems desirable to be used in particular as a detection device that detects a physical quantity of intake air of a vehicle, and obtains various effects. One of the various problems solved by the following embodiment is the contents described in the column of the problem to be solved by the invention, and one of various effects obtained by the following embodiment is the effect described in the column of the effect of the invention. Various problems solved by the following embodiment and various effects obtained by the following embodiment will be described in the description of the following embodiment. Thus, the problems and effects solved by the embodiment and described in the following embodiment are also described in contents other than the contents in the column of the problem to be solved by the invention and the effects in the column of the invention.

In the following embodiment, the same reference numerals indicate the same configuration even if the figure numbers are different from each other, and the same effects are obtained. For the configuration that is already described, only the reference numeral is attached to the drawing, and sometimes the description is omitted.

FIG. 1 is a system diagram illustrating an embodiment in which a physical quantity detection device according to the present invention is used in an electronic fuel injection type internal combustion engine control system 1. Based on operation of an internal combustion engine 10 including an engine cylinder 11 and an engine piston 12, intake air is sucked from an air cleaner 21 as a measured gas 2, and led to a combustion chamber of the engine cylinder 11 through an intake body that is, for example, a main passage 22, a throttle body 23, and an intake manifold 24. A physical quantity of the measured gas 2 that is intake air led to the combustion chamber is detected by a physical quantity detection device 20 of the present invention, and fuel is supplied from a fuel injection valve 14 based on the detected physical quantity, and led to the combustion chamber in a state of air-fuel mixture together with the measured gas 2. In the embodiment, the fuel injection valve 14 is provided in an intake port of the internal combustion engine, and the fuel injected into the intake port forms an air-fuel mixture together with the measured gas 2, is led to the combustion chamber through an intake valve 15, and burns and generates mechanical energy.

The fuel and air guided to the combustion chamber are in a mixed state of fuel and air, and are explosively burned by spark ignition of a spark plug 13 to generate the mechanical energy. The combusted gas is led from an exhaust valve 16 to an exhaust pipe, and exhausted as exhaust gas 3 from the exhaust pipe to an outside of a vehicle. A flow rate of the measured gas 2 that is the intake air led to the combustion chamber is controlled by a throttle valve 25 in which an opening degree changes based on operation of an accelerator pedal. The fuel supply amount is controlled based on the flow rate of the intake air led to the combustion chamber, and a driver controls the flow rate of the intake air led to the combustion chamber by controlling the opening degree of the throttle valve 25, whereby the driver can control the mechanical energy generated by the internal combustion engine.

<Outline of Control of Internal Combustion Engine Control System>

The physical quantity detection device 20 detects the physical quantity such as the flow rate, temperature, humidity, and pressure of the measured gas 2 that is the intake air taken in from the air cleaner 21 and flows through the main passage 22, and inputs an electric signal representing the physical quantity of the intake air to a control device 4. Output of a throttle angle sensor 26 that measures the opening degree of the throttle valve 25 is input to the control device 4, and a position and a state of the engine piston 12, the intake valve 15, or the exhaust valve 16 of the internal combustion engine are input to the control device 4. Additionally, a rotating speed of the internal combustion engine, and output of a rotation angle sensor 17 are input to the control device 4 in order to measure the rotating speed. The output of an oxygen sensor 28 is input to the control device 4 in order to measure the state of the mixture ratio of a fuel amount and an air amount from the state of the exhaust gas 3.

The control device 4 calculates a fuel injection amount and ignition timing based on the physical quantity of the intake air that is the output of the physical quantity detection device 20 and the rotating speed of the internal combustion engine that is measured based on the output of the rotation angle sensor 17. The amount of fuel supplied from the fuel injection valve 14 and the ignition timing ignited by the spark plug 13 are controlled based on the calculation results. The fuel supply amount and the ignition timing are finely controlled based on the temperature, a change state of a throttle angle, and a change state of the engine rotating speed, which are detected by the physical quantity detection device 20 and the state of the air-fuel ratio measured by the oxygen sensor 28. The control device 4 further controls the amount of air that bypasses the throttle valve 25 using an idle air control valve 27 in an idle operation state of the internal combustion engine, thereby controlling the rotating speed of the internal combustion engine in the idle operation state.

Both the fuel supply amount and the ignition timing, which are main controlled variables of the internal combustion engine, are calculated using the output of the physical quantity detection device 20 as a main parameter. Thus, improvement in detection accuracy of the physical quantity detection device 20, prevention of a change with time, and improvement of reliability are important in terms of improvement of control accuracy of the vehicle and a guarantee of the reliability.

In particular, in recent years, there are a very high demand for fuel efficiency of the vehicle and a very high demand for purification of an exhaust gas. In order to meet these demands, it is extremely important to improve the detection accuracy of the physical quantity of the intake air 2 detected by the physical quantity detection device 20. It is also important that the physical quantity detection device 20 maintains the high reliability.

The vehicle on which the physical quantity detection device 20 is mounted is used in an environment in which temperature and humidity change largely. It is desirable for the physical quantity detection device 20 to take into account a response to the changes in temperature and humidity in a usage environment and a response to dust and pollutants.

The physical quantity detection device 20 is attached to an intake pipe that is affected by heat generated by the internal combustion engine. For this reason, the heat generated by the internal combustion engine is transmitted to the physical quantity detection device 20 through the intake pipe that is the main passage 22. Because the physical quantity detection device 20 detects a flow rate of the measured gas by performing heat transfer with the measured gas, it is important to prevent the influence of the heat from the outside as much as possible.

As described below, not only the physical quantity detection device 20 mounted on the vehicle simply solves the problem described in the column of the problem to be solved by the invention and only obtains the effect described in the column of the effect of the invention, but also the physical quantity detection device 20 solves various problems required as a product are solved and obtains various effects in sufficient consideration of the various problems described above. Specific problems to be solved and specific effects to be obtained by the physical quantity detection device 20 will be described in the description of the following embodiment.

<Appearance Structure of Physical Quantity Detection Device>

FIGS. 2A to 2F are views illustrating the appearance of the physical quantity detection device. In the following description, it is assumed that the measured gas flows along a center axis of the main passage.

The physical quantity detection device 20 is used by being inserted into the main passage 22 from an attachment hole made in a passage wall of the main passage 22. The physical quantity detection device 20 includes a housing 201 and a cover 202 attached to the housing 201. The housing 201 is formed by injection molding of a synthetic resin material, and the cover 202 is formed by a plate-shaped member made of a conductive material such as an aluminum alloy. The cover 202 is formed in a thin plate shape, and includes a wide flat cooling surface.

The housing 201 includes a flange 211 fixing the physical quantity detection device 20 to the intake body that is the main passage 22, a connector 212 that protrudes from the flange 211 and is exposed to the outside from the intake body for electrical connection to an external device, and a measuring unit 213 extending from the flange 211 so as to protrude toward the center of the main passage 22.

The measuring unit 213 has a thin and long shape extending from the flange 211 toward the center of the main passage 22, and has a wide front face 221 and back face 222 and a pair of narrow side faces 223, 224. The measuring unit 213 protrudes from the inner wall of the main passage 22 toward the passage center of the main passage 22 with the physical quantity detection device 20 attached to the main passage 22. The front face 221 and the back face 222 are disposed in parallel along the center axis of the main passage 22, the side face 223 on one side in a short-side direction of the measuring unit 213 in the narrow side faces 223, 224 of the measuring unit 213 is disposed opposite an upstream side of the main passage 22, and the side face 224 on the other side in the short-side direction of the measuring unit 213 is disposed opposite a downstream side of the main passage 22.

Figure 2A:
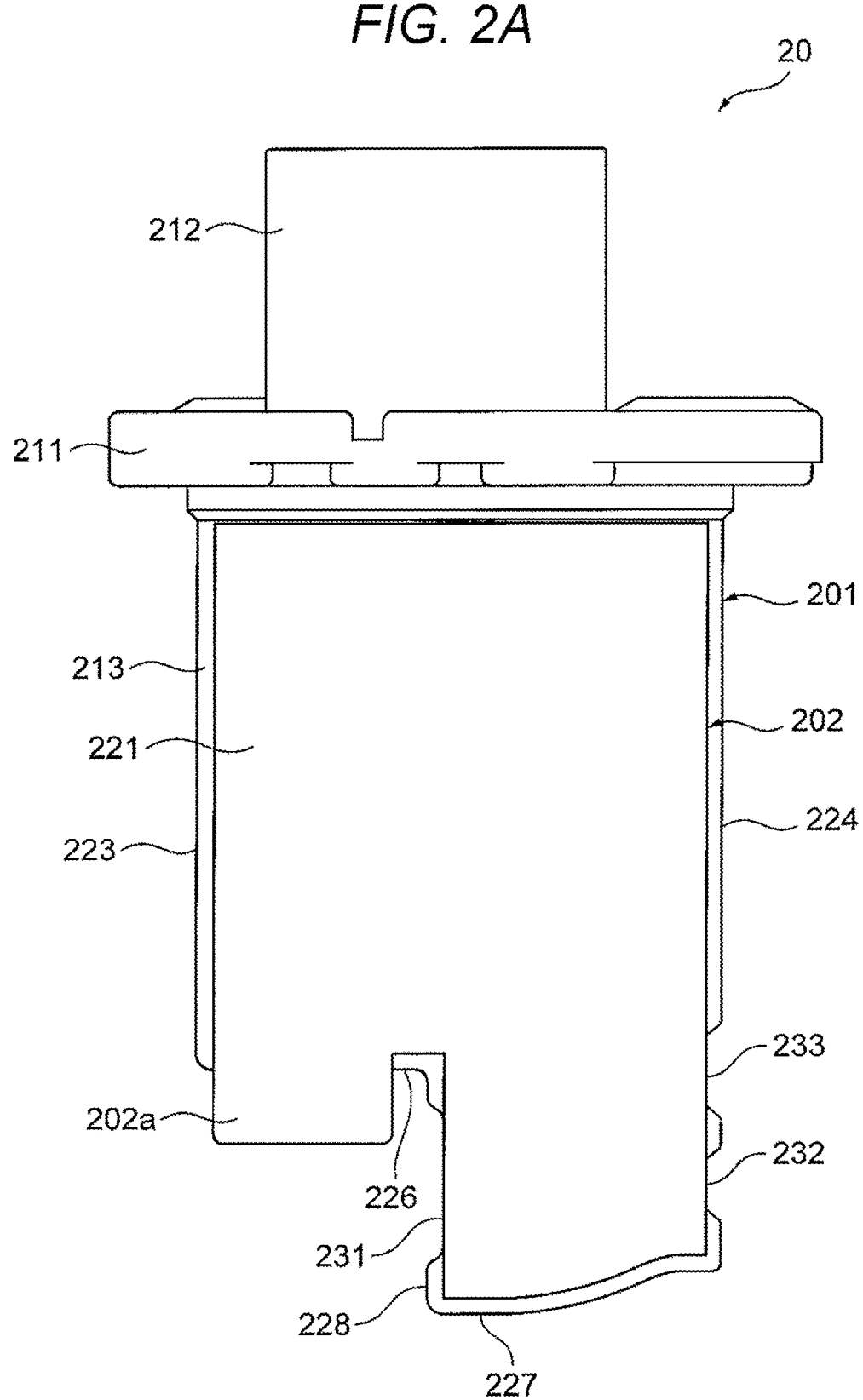
FIG. 2A is a front view of the physical quantity detection device.
Figure 2B:
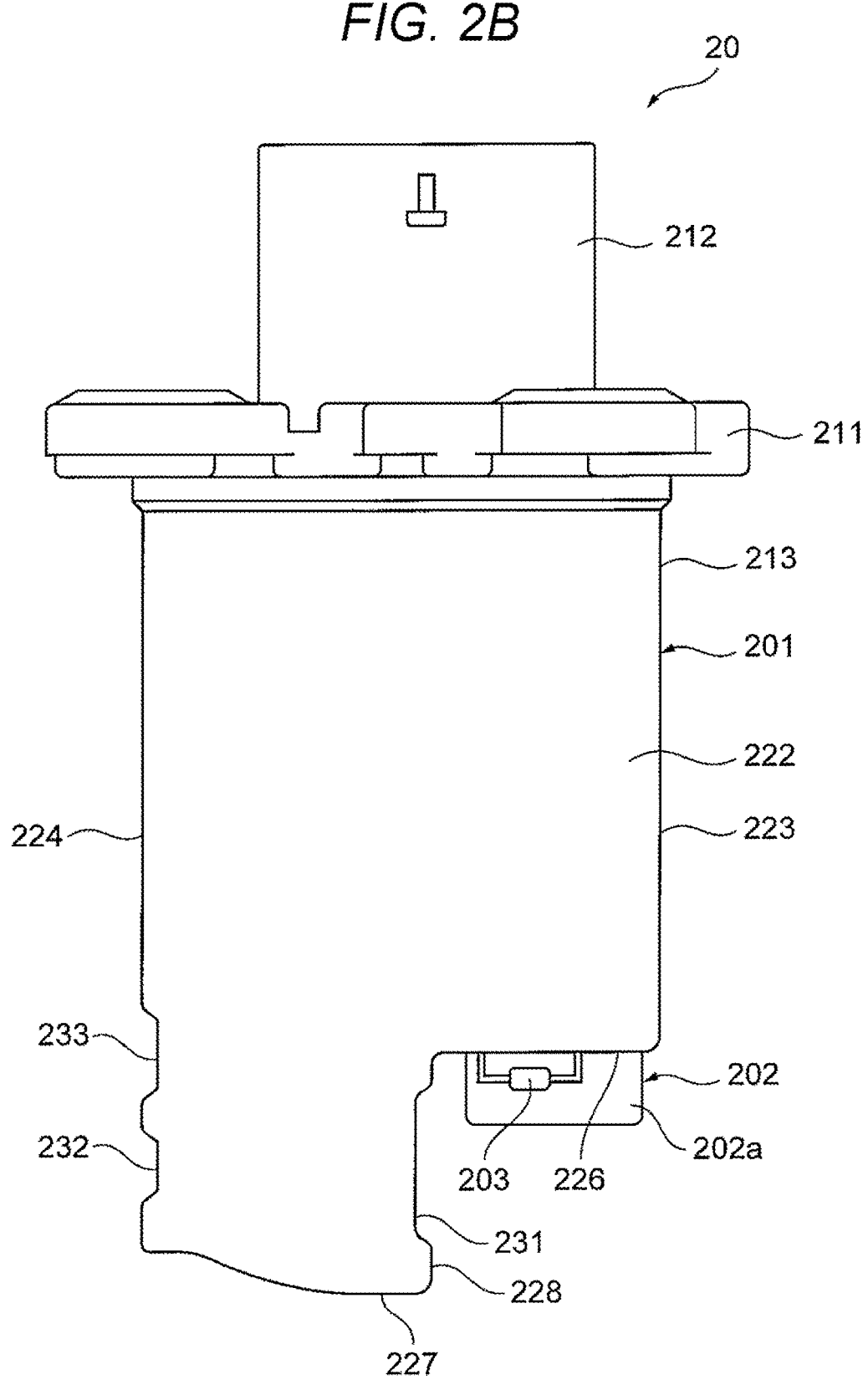
FIG. 2B FIG. 2B is a rear view of the physical quantity detection device.
Figure 2C:
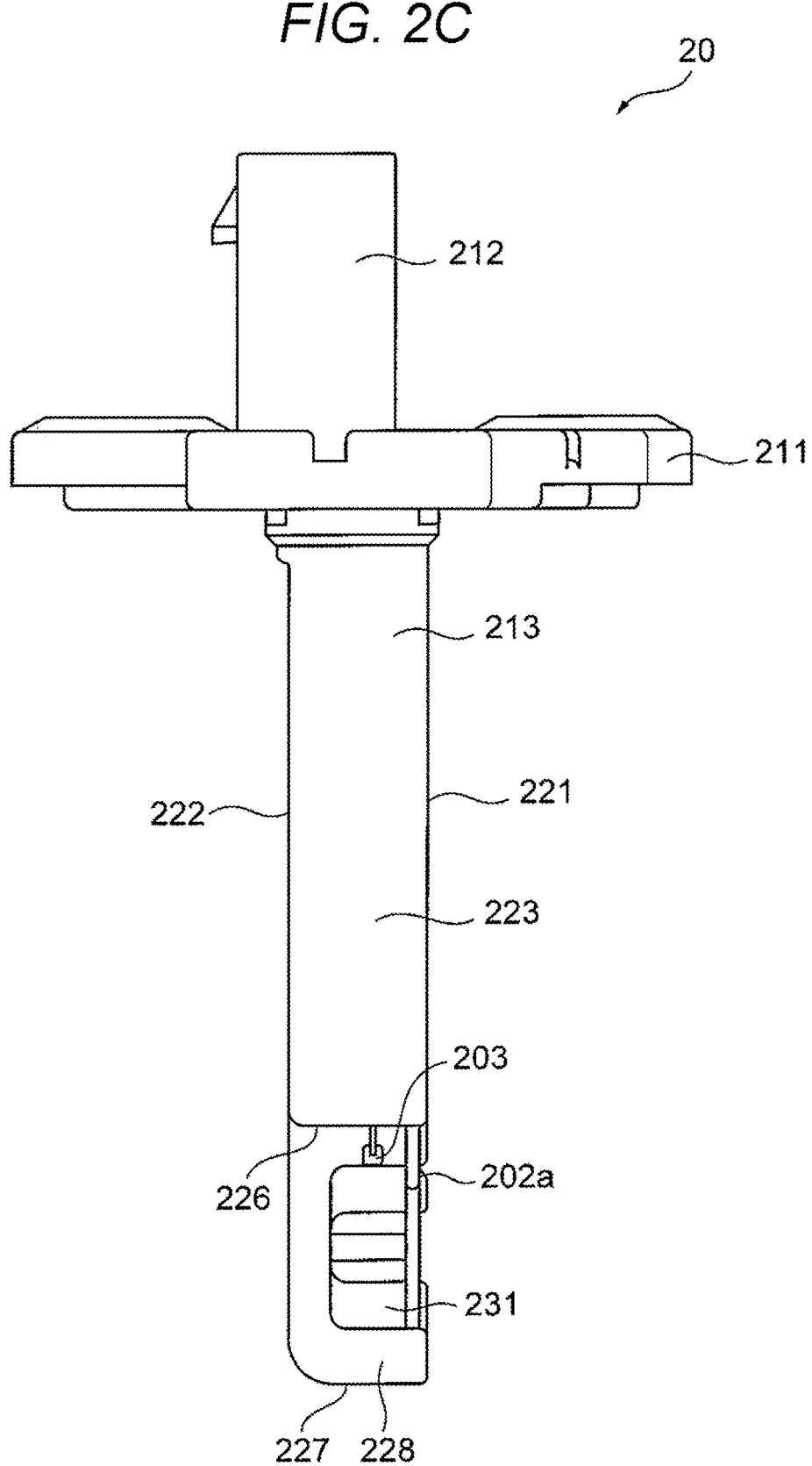
FIG. 2C is a left side view of the physical quantity detection device.
Figure 2D:
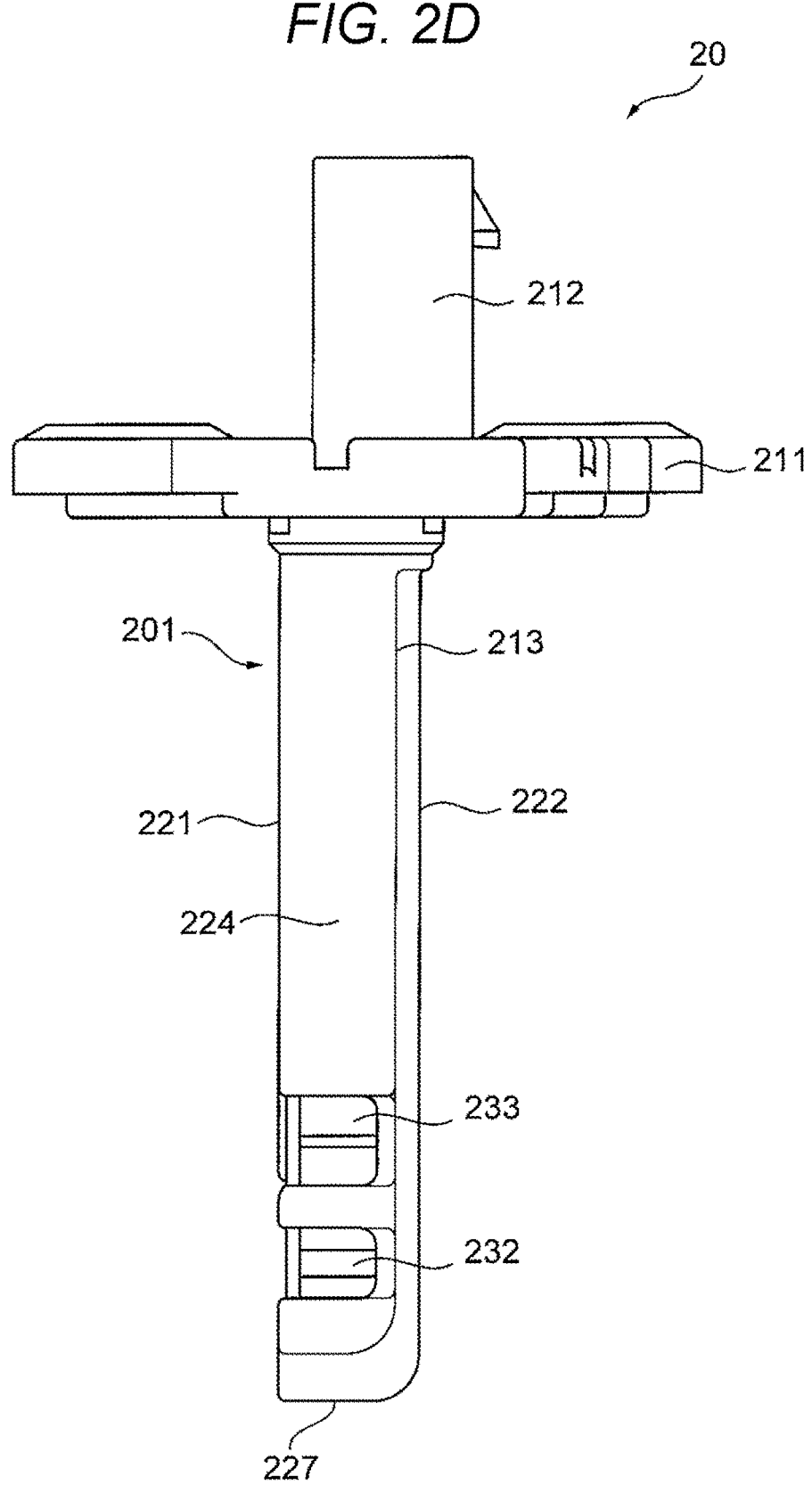
FIG. 2D is a right side view of the physical quantity detection device.
Figure 2E:
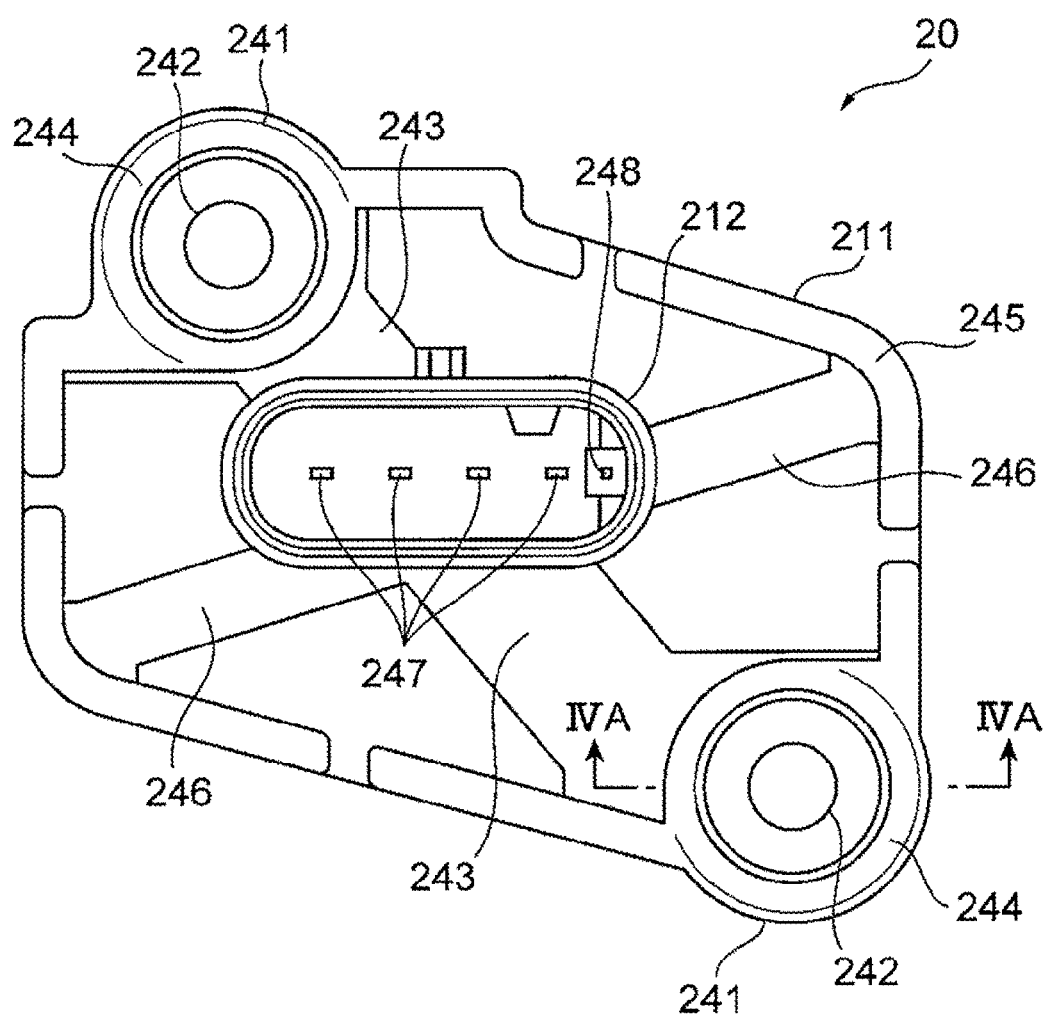
FIG. 2E is a plan view of the physical quantity detection device.
Figure 2F:
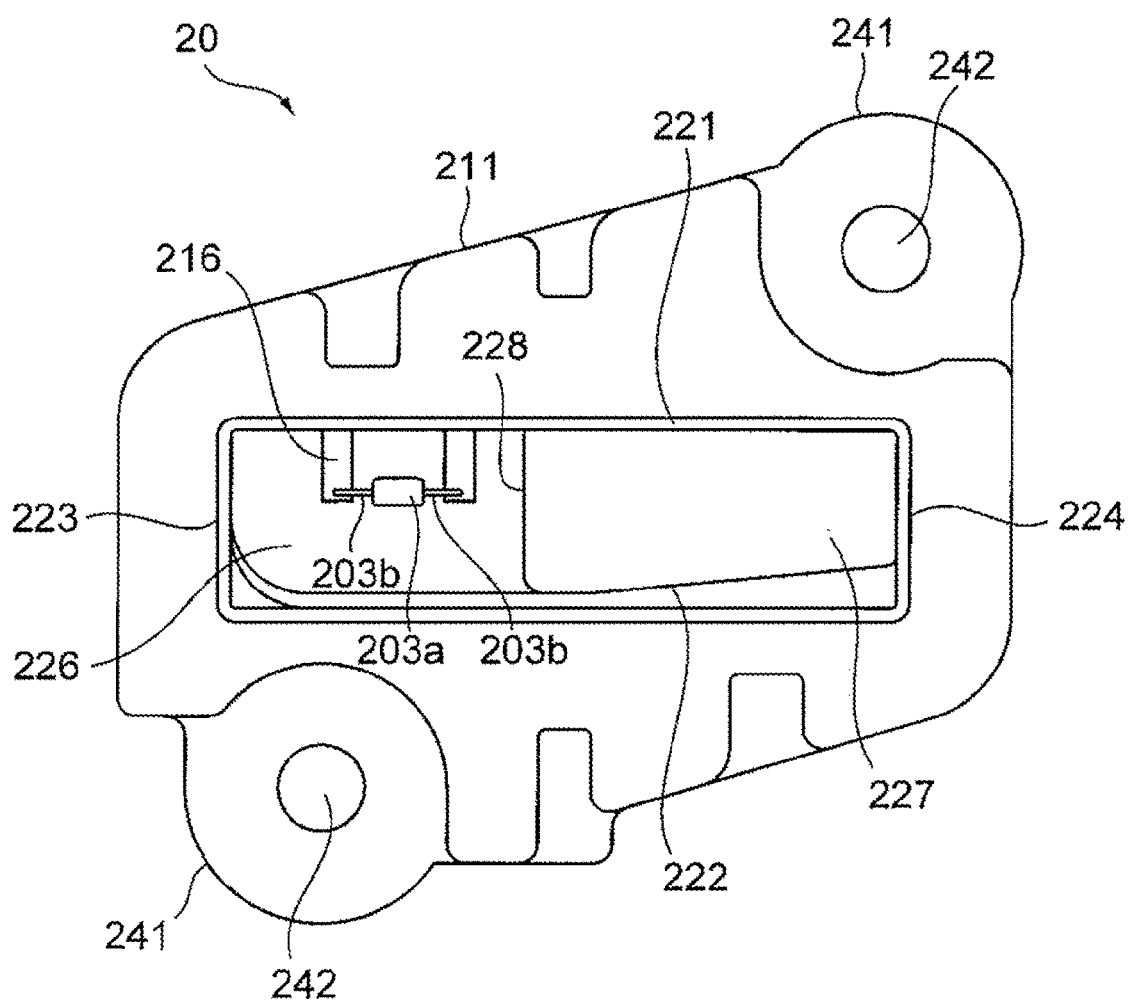
FIG. 2F is a bottom view of the physical quantity detection device.

As illustrated in FIG. 2F, while the front face 221 of the measuring unit 213 is flat from the side face 223 on one side to the side face 224 on the other side along the short-side direction, the back face 222 of the measuring unit 213 includes a chamfered corner, and is inclined in a direction gradually approaching the front as it moves from an intermediate position in the short-side direction to the side face 224 on the other side, and has a sectional shape of what is called a streamline type. Thus, the measured gas 2 flowing from the upstream side of the main passage 22 can be smoothly led downstream along the front face 221 and the back face 222, and fluid resistance to the measured gas 2 can be reduced.

In the leading edge of the measuring unit 213, the bottom surface of the measuring unit 213 is formed stepwise. The leading edge of the measuring unit 213 includes a bottom surface 226 on one side disposed on the upstream side of the main passage 22 with the physical quantity detection device 20 attached to the main passage 22 and a bottom surface 227 on the other side disposed on the downstream side of the main passage 22, the bottom surface 227 on the other side protrudes from the bottom surface 226 on one side, and a step surface 228 connecting the bottom surface 226 on one side and the bottom surface 227 the other side is disposed toward the upstream side of the main passage 22. An inlet 231 is provided in the step surface 228 of the measuring unit 213 in order to take part of the measured gas 2 such as intake air into the sub-passage in the measuring unit 213. A first outlet 232 and a second outlet 233, which return the measured gas 2 taken in the sub-passage in the measuring unit 213 to the main passage 22, are provided at a position located in the side face 224 on the other side in the short-side direction of the measuring unit 213 and opposed to the step surface 228.

That is, the measuring unit 213 includes a first wall (the side face 223 on one side) disposed toward the upstream side in a flow direction of the measured gas 2 in the main passage 22 and a second wall (step surface 228) disposed toward the upstream side in a flow direction of the measured gas 2 in the main passage 22 at the position on a leading edge side of the measuring unit 213 with respect to the first wall and on the downstream side in the flow direction of the measured gas 2 in the main passage 22.

An inlet 231 of the sub-passage is open to the second wall.

In the physical quantity detection device 20, the inlet 231 of the sub-passage is provided at the leading edge of the measuring unit 213 extending from the flange 211 toward the center direction of the main passage 22, so that not the gas in a vicinity of the inner wall surface of the main passage 22 but the gas near the center portion separating from the wall surface can be taken in the sub-passage. For this reason, the physical quantity detection device 20 can measure the flow rate of the gas in a portion separating from the inner wall surface of the main passage 22, and can prevent degradation of the measurement accuracy due to the influence of heat or the like.

In the vicinity of the inner wall surface of the main passage 22, the measurement is easily affected by the temperature of the main passage 22, and the temperature of the measured gas 2 is different from the original temperature of the gas and different from an average state of the main gas in the main passage 22. In particular, when the main passage 22 is the intake body of the engine, the intake body is often maintained at a high temperature due to the influence of the heat from the engine. For this reason, the gas in the vicinity of the inner wall surface of the main passage 22 is often higher than the original temperature of the main passage 22, which causes the degradation of the measurement accuracy. The fluid resistance is large near the inner wall surface of the main passage 22, and a flow speed is lower than an average flow speed of the main passage 22. For this reason, when the gas in the vicinity of the inner wall surface of the main passage 22 is taken in the sub-passage as the measured gas 2, there is a risk that a decrease in flow speed with respect to the average flow speed of the main passage 22 leads to a measurement error.

In the physical quantity detection device 20, the inlet 231 is provided at the leading edge of the thin and long measuring unit 213 extending from the flange 211 toward the center of the main passage 22, so that the measurement error associated with the decrease in flow speed near the inner wall surface can be reduced. In the physical quantity detection device 20, not only the inlet 231 is provided at the leading edge of the measuring unit 213 extending from the flange 211 toward the center of the main passage 22, but also the first outlet 232 and the second outlet 233 of the sub-passage are also provided at the leading edge of the measuring unit 213, so that the measurement error can further be reduced.

Although the physical quantity detection device 20 has the shape in which the measuring unit 213 extends long along the axis from the outer wall of the main passage 22 toward the center, widths of the side faces 223, 224 are formed in a narrow shape as illustrated in FIGS. 2C and 2D. Consequently, the physical quantity detection device 20 can suppress the fluid resistance to a small value with respect to the measured gas 2.

<Structure of Temperature Detector>

In the physical quantity detection device 20, as illustrated in FIG. 2B, an intake air temperature sensor 203 that is a temperature detector is provided at the leading edge of the measuring unit 213. The intake air temperature sensor 203 is provided so as to be exposed to the outside of the measuring unit 213. Specifically, in the flow direction of the measured gas 2, the intake air temperature sensor 203 is disposed at the position on the downstream side of the side face on one side of the measuring unit 213 and the upstream side of the step surface 228 of the measuring unit 213. The inlet 231 of the sub-passage is provided in the step surface 228 of the measuring unit 213, and the intake air temperature sensor 203 is disposed on the upstream side of the inlet 231 of the sub-passage.

The intake air temperature sensor 203 is provided so as to be exposed to the outside of the measuring unit 213 and disposed on the upstream side of the inlet 231 of the sub-passage, so that the intake air temperature sensor 203 has a little influence on flow rate measurement of a flow sensor 205 provided in the sub-passage as compared with the case where the intake air temperature sensor 203 is disposed in the sub-passage of the measuring unit 213.

The intake air temperature sensor 203 is constructed with an axial lead component including a columnar sensor body 203a and a pair of leads 203b protruding from both ends in an axial direction of the sensor body 203a toward a direction in which the leads 203b separate from each other. The intake air temperature sensor 203 is mounted on a circuit board 207 in the measuring unit 213 with a lead 203b interposed therebetween, the pair of leads 203b protrudes from the bottom surface 226 on one side of the measuring unit 213, and the sensor body 203a is disposed at the position opposed to the step surface 228 of the measuring unit 213. The intake air temperature sensor 203 is disposed in a direction along the bottom surface 226 on one side of the measuring unit 213 and the flow direction of the measured gas 2.

Because the intake air temperature sensor 203 is exposed to the outside of the measuring unit 213 while the sensor body 203a is supported by the pair of leads 203b, preferably a protector 202a protecting the intake air temperature sensor 203 is formed in the measuring unit 213. The protector 202a is disposed on the front side of the measuring unit 213 with respect to the intake air temperature sensor 203 while protruding from the bottom surface of the measuring unit 213.

In the embodiment, by way of example, a part of the cover 202 protrudes from the bottom surface of the measuring unit 213. Alternatively, the cover 202 may have a shape protruding toward the housing 201. By providing the protector 202a, the intake air temperature sensor 203 can be prevented from contacting directly with other objects during transportation of working of the physical quantity measuring device.

The protector 202a also functions as a rectification member exhibiting a rectification effect, whereby turbulence of the flow due to the fluid colliding with the intake air temperature sensor 203 can be prevented. For this reason, the turbulence of the flow can be prevented from entering the sub-passage 234 in which the flow sensor 205 is mounted, and the influence on the flow sensor 205 can be prevented when the intake air temperature sensor 203 is disposed on the upstream side of the inlet 231 of the sub-passage 234. In particular, when improvement of a response is achieved by providing the sensor body 203a of the intake air temperature sensor 203 in an opening projection surface of the inlet 231 where the flow is fast, because the turbulence of the flow invades easily into the sub-passage, more preferably the rectification is performed to prevent the turbulence of the flow in order to balance the accuracy of the flow sensor 205 and the accuracy of the intake air temperature sensor 203 with each other.

A protrusion length of the protector 202a can arbitrarily be selected. For example, when the intake air temperature sensor 203 is disposed far away from the bottom surface 226 on one side of the measuring unit 213, the protrusion length is set such that the leading edge of the protector 202a is disposed at least up to the same position as the intake air temperature sensor 203. When the intake air temperature sensor 203 is disposed in the vicinity of the bottom surface 226 on one side of the measuring unit 213, the protector may not be provided because a possibility that the intake air temperature sensor 203 contacts with another object decreases as compared with the case where the intake air temperature sensor 203 is disposed far away from the bottom surface 226.

The measuring unit 213 includes the side face 223 on one side (first wall) disposed toward the upstream side in a flow direction of the measured gas 2 in the main passage 22 and the step surface 228 (second wall) disposed toward the upstream side in a flow direction of the measured gas 2 in the main passage 22 at the position on a leading edge side of the measuring unit 213 with respect to the side face 223 on one side and on the downstream side in the flow direction of the measured gas 2 in the main passage 22, the inlet 231 of the sub-passage being open to the step surface 228. In other words, the inlet 231 of the sub-passage 234 is provided on the leading edge side (the opposite side to the flange 211) and on the downstream side of the first wall 223.

The intake air temperature sensor 203 is located on the downstream side in the flow direction of the measured gas 2 in the main passage 22 with respect to the side face 223 on one side and on the upstream side in the flow direction of the measured gas 2 in the main passage 22 with respect to the inlet 231 of the sub-passage open to the step surface 228 (second wall).

A separated flow flowing toward the step surface 228 of the measuring unit 213 is generated when the measured gas 2 flowing in the main passage 22 collides with the side face 223 on one side. As compared with the flow in the side face 223 on one side, the flow on the downstream side and the leading edge side is accelerated by the separated flow.

The intake air temperature sensor 203 is disposed in a region corresponding to the increased flow, so that responsiveness can be improved.

FIG. 3 illustrates the measurement of the flow speed of the measured gas around the physical quantity detection device.

According to the measurement result, the flow speed was less than or equal to 0.5 m/s at points (8) to (14) on the upstream side of the side face 223 on one side of the measuring unit 213, the flow speed was greater than or equal to 0.6 m/s one side of the measuring unit 213 at points (1) to (7) on the downstream side of the side face 223 and on the upstream side of the step surface 228 of the measuring unit 213, and the flow speed at the position on the downstream side of the side face 223 on one side of the measuring unit 213 and on the upstream side of the step surface 228 of the measuring unit 213 was higher the flow speed at the position on the upstream side of the side face 223 on the one side of the measuring unit 213. This is because the separated flow generated by the collision of the measured gas 2 with the side face 223 on one side of the measuring unit 213 increases the flow of the measured gas 2 at the position on the downstream side of the side face 223 on one side of the measuring unit 213 and on the upstream side of the step surface 228 of the measuring unit 213.

At the points (2) to (7) located on the projection surface of the inlet 231, the flow speed is greater than or equal to 0.7 m/s, and the flow becomes faster. This is presumed to be a result of the flow of the fluid becoming easier due to the decrease in resistance of the fluid because the wall that becomes an obstacle does not exist on the downstream side.

The particularly excellent results were obtained at the points (2) and (3), at which the influence of the speed increase due to the separation by the first wall 223 is easily generated and the obstacle that becomes the fluid resistance does not exist on the downstream side.

According to the physical quantity detection device 20 of the embodiment, the intake air temperature sensor 203 is disposed not at the position on the upstream side of side face 223 on one side of the measuring unit 213 but at the position on the downstream side of the side face 223 on one side of the measuring unit 213 and on the upstream side of the step surface 228 of the measuring unit 213, so that not only the measured gas 2 flowing straight from the upstream but also the separated flow can collide with the intake air temperature sensor 203. Thus, heat dissipation of the intake air temperature sensor 203 can be improved.

More preferably, the flow deceleration can be prevented when the sensor body 203a is located on an inlet projection plane. In this case, when the rectification member (protector) is provided, more preferably trade-off with the accuracy of the flow sensor 205 is satisfied because the disturbance of the fluid invading into the sub-passage 234 can be prevented.

In the embodiment, a speed increasing region is formed on the upstream side of an inlet 231 of the sub-passage 234 in a limited mounting space, and the intake air temperature sensor 203 is mounted in the speed increasing region, so that the downsizing can be achieved while the accuracy is maintained and improved. The acceleration of the air taken in the sub-passage 234 and the acceleration of the air colliding with the intake air temperature sensor 203 are simultaneously performed by the first wall 223, which contributes to space saving.

<Structure of Flange>

The measuring unit 213 of the physical quantity detection device 20 is inserted into the inside through an attachment hole made in the main passage 22, and the flange 211 of the physical quantity detection device 20 abuts on the main passage 22, and is fixed to the main passage 22 using a screw. The flange 211 has a substantially rectangular shape in planar view having a predetermined plate thickness, and as illustrated in FIGS. 2E and 2F, a pair of fixing holes 241 are made at diagonal corners. The fixing hole 241 includes a through-hole 242 piercing the flange 211. The flange 211 is fixed to the main passage 22 by inserting a fixing screw (not illustrated) into the through-hole 242 of the fixing hole 241 to screw the flange 211 to the main passage 22.

As illustrated in FIG. 2E, a plurality of ribs are provided in the top surface of the flange 211. The ribs include a first rib 243 linearly connecting the fixing hole 241 and the connector 212, a second rib 244 having a tapered section shape surrounding a periphery of the through-hole 242 of the fixing hole 241, a third rib 245 provided along an outer periphery of the flange 211, and a fourth rib 246 extending in a direction intersecting the first rib 243 on a diagonal line of the flange 211.

The first rib 243 has a high flange reinforced effect because the first rib 243 is linearly provided between the fixing hole 241 in which screw fixing force acts on the main passage 22 and the connector 212 having relatively high rigidity due to the three-dimensional shape. Thus, a thickness of the flange 211 can be decreased as compared with the case where the first rib 243 is not provided, a weight of the whole housing can be reduced, and the influence of the shrinkage of the resin constituting the flange 211 can be reduced during the molding of the housing 201.

Figure 4A:
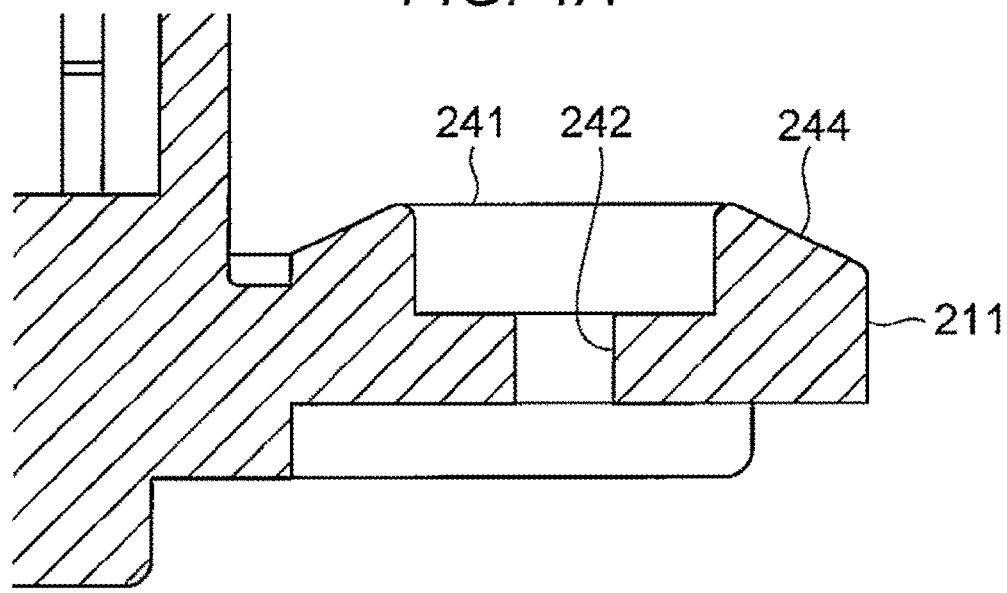
FIG. 4A is a sectional view taken along a line IVA-IVA in FIG. 2E.
Figure 4B:
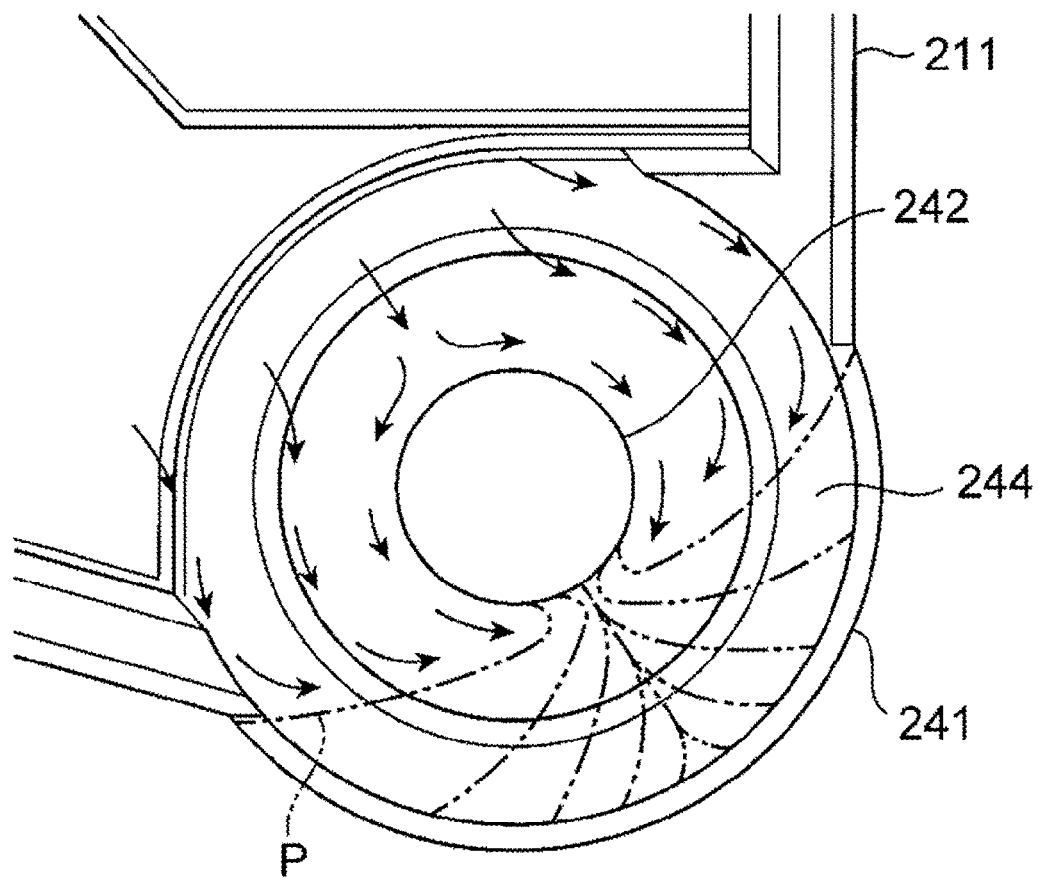
FIG. 4B is a view illustrating a flow of resin during resin molding in a flange of the embodiment.
Figure 5A:
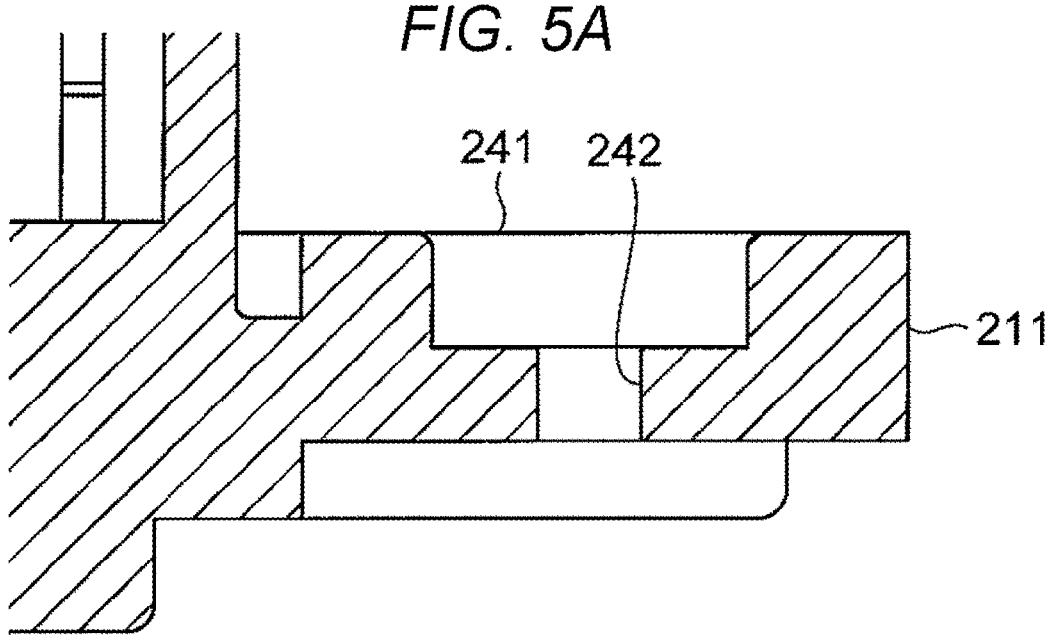
FIG. 5A is a view corresponding to FIG. 4A in a comparative example.
Figure 5B:
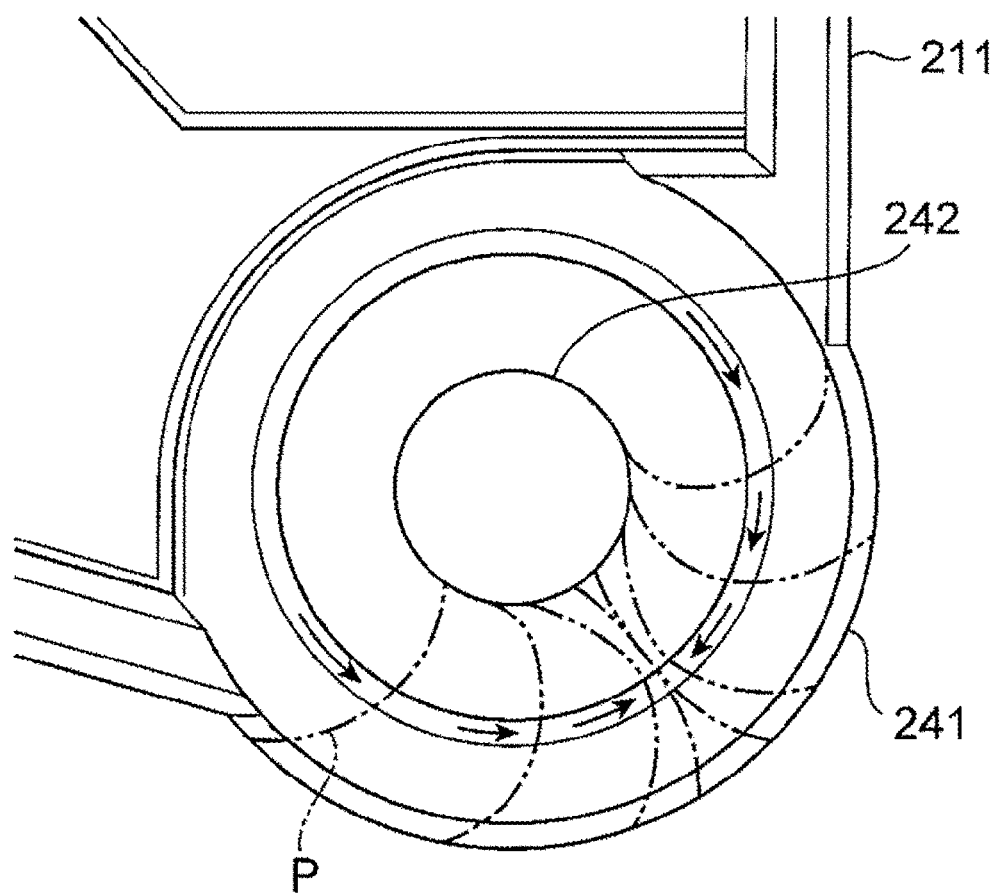
FIG. 5B is a view illustrating the flow of the resin during the resin molding in a flange of the comparative example.

FIG. 4A is a sectional view taken along a line IVA-IVA in FIG. 2E, FIG. 4B is a view illustrating the flow of the resin during the resin molding in the flange of the embodiment, and FIG. 5A is a view corresponding to FIG. 4A in the comparative example, and FIG. 5B is a view illustrating the flow of the resin during the resin molding in the flange of the comparative example.

The housing 201 is manufactured by injection molding a resin in a forming die, and resin P flows in the forming die so as to go around the through-hole 242 in the flange 211 during the resin molding. For example, the flow of the resin P is hardly controlled when the thickness around the through-hole 242 of the fixing hole 241 is uniform as illustrated in FIG. 5A, a central portion in the width direction advances at the head and as illustrated in FIG. 5B when the resin P flows from both sides of the through-hole 242 while being separated into two at the portion of the through-hole 242, and the central portions in the width direction are initially merged together, and the merge gradually proceeds toward the direction approaching the through-hole 242 and the direction separating from the through-hole 242. Thus, there is a risk that a weak weld (resin merge portion) in which the merge of the resin P is insufficient is generated in the merge portion, and there is a possibility that durability is low and a crack is generated when a metal bush is not used.

On the other hand, in the embodiment, the second rib 244 having the tapered shape in section is provided around the through-hole 242 as illustrated in FIG. 4A. In the second rib 244, as illustrated in FIG. 4B, when the resin P flows from both sides of the through-hole 242 while being bifurcated at the portion of the through-hole 242, the flow of the resin P is controlled such that the merge is first performed with the portion near the through-hole in the width direction of the flowing resin P as the head, and such that the merge proceeds only toward the direction separating from the through-hole 242. Thus, the resin P can sufficiently be merged in the merge portion, and the generation of the weak weld can be prevented.

The first rib 243 is linearly provided along the diagonal line connecting the pair of fixing holes 241, and the fourth rib 246 is provided along the other diagonal line. The first rib 243 is formed relatively thick compared to the fourth rib 246, and has high rigidity. In the third rib 245, a notch is provided for each side of the flange 211 so as to prevent the liquid from accumulating in the region that is the top surface of the flange 211 and is surrounded by the first rib 243 and the third rib 245.

As illustrated in FIG. 2E, four external terminals 247 and correction terminals 248 are provided in the connector 212. The external terminal 247 is a terminal outputting the physical quantity, such as a flow rate or temperature, which is a measurement result of the physical quantity detection device 20, and a power supply terminal supplying DC power operating the physical quantity detection device 20. The correction terminal 248 is a terminal used to measure the manufactured physical quantity detection device 20, obtain a correction value associated with each physical quantity detection device 20, and store the correction value in a memory of the physical quantity detection device 20. In the subsequent measurement operation of the physical quantity detection device 20, correction data representing the correction value stored in the memory is used, but the correction terminal 248 is not used. Thus, the correction terminal 248 has a shape different from that of the external terminal 247 such that the correction terminal 248 does not become an obstacle when the external terminal 247 is connected to another external device. In the embodiment, the correction terminal 248 is shorter than the external terminal 247, and the correction terminal 248 does not interfere with the connection even if the connection terminal to the external device connected to the external terminal 247 is inserted into the connector 212.

<Structure of Housing>

Figure 6A:
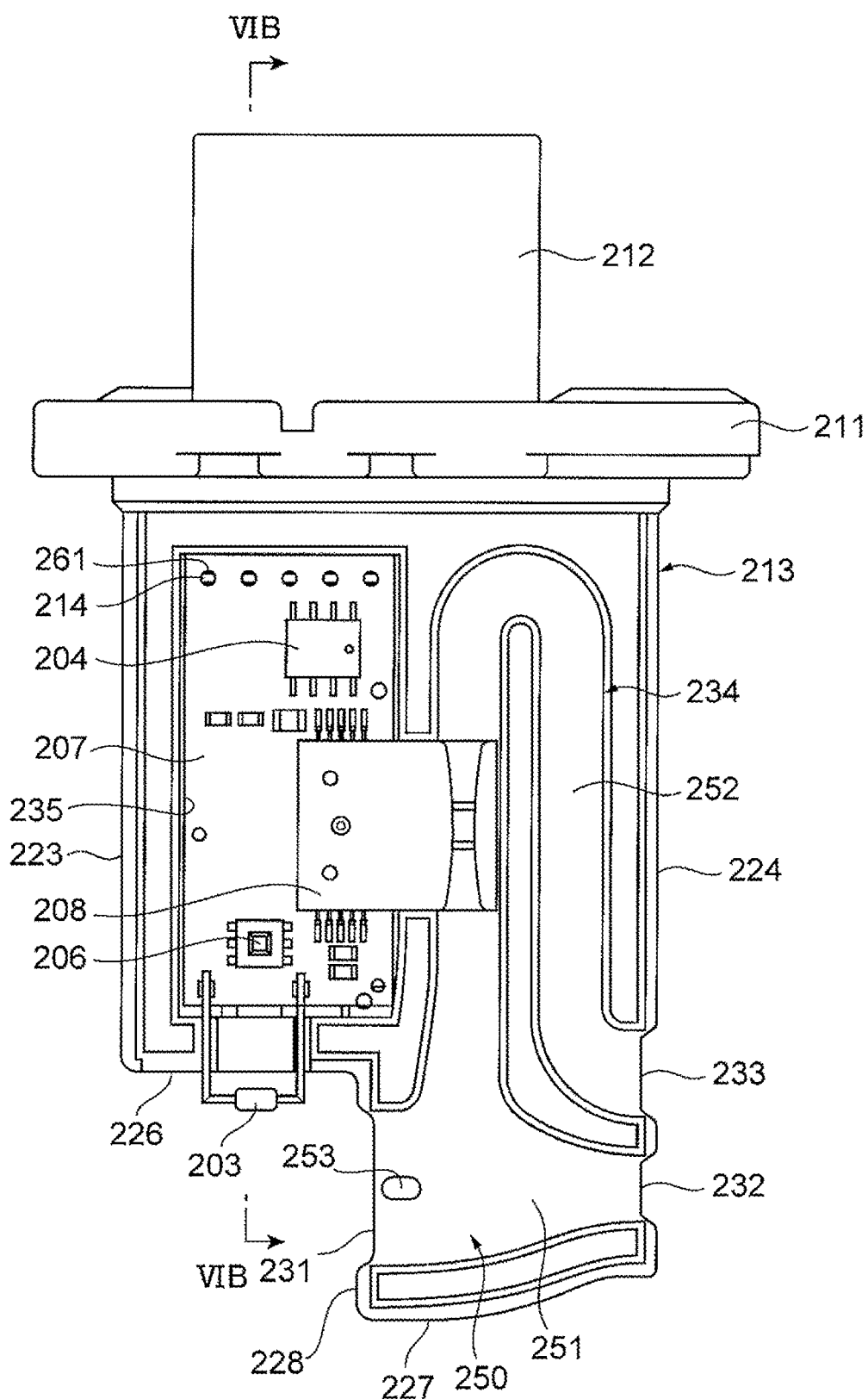
FIG. 6A is a front view of a housing with a cover removed.
Figure 6B:
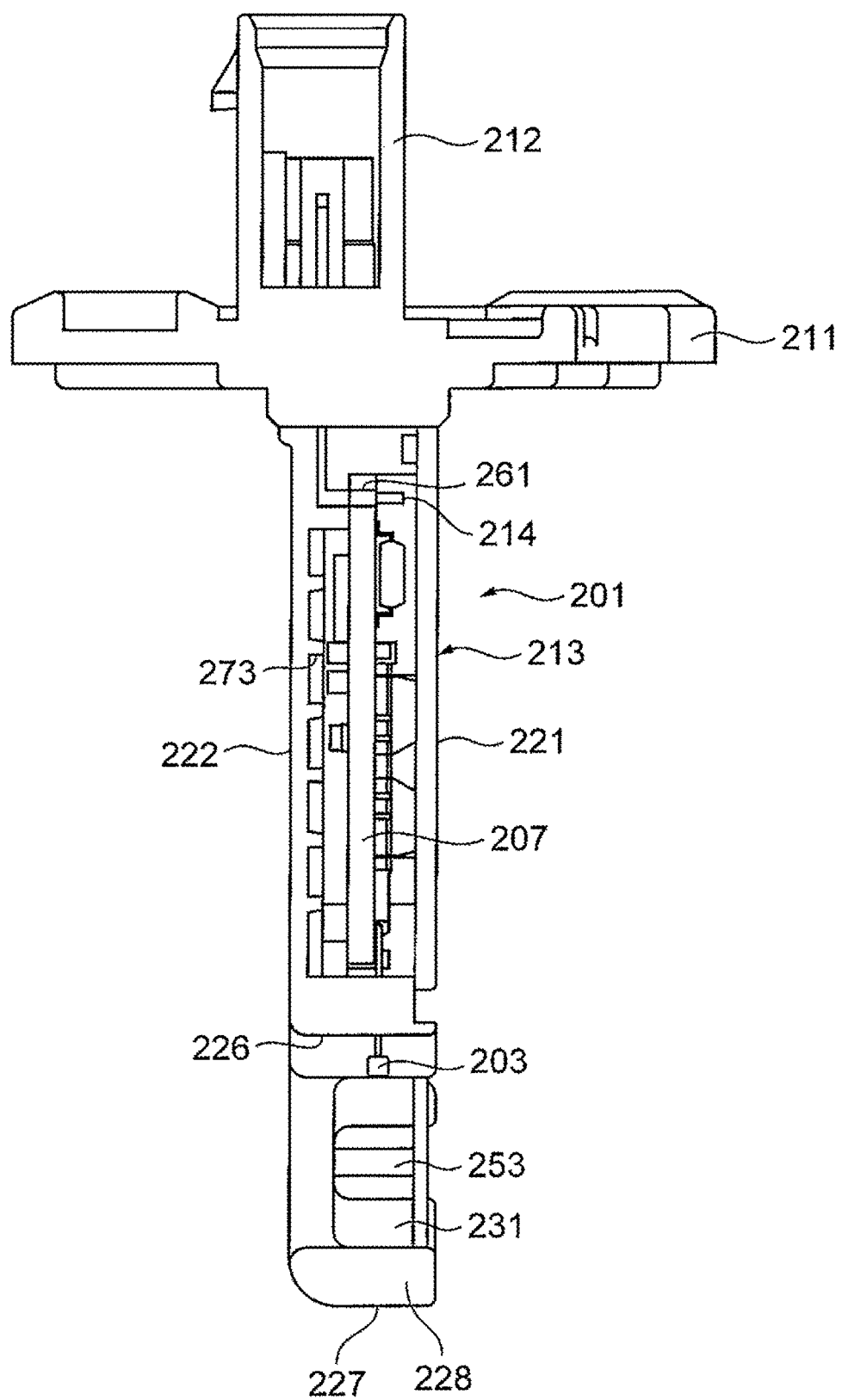
FIG. 6B is a sectional view taken along a line VIB-VIB in FIG. 6A.

FIG. 6A is a front view of the housing with the cover removed, and FIG. 6B is a sectional view taken along a line VIB-VIB in FIG. 6A. A sealing member sealing the circuit board is omitted in FIGS. 6A and 6B.

A sub-passage groove 250 forming the sub-passage 234 in the measuring unit 213 and a circuit chamber 235 accommodating the circuit board 207 are provided in the housing 201. The circuit chamber 235 and the sub-passage groove 250 are recessed in the front of the measuring unit 213, and disposed separately on one side and the other side in the short-side direction of the measuring unit 213.

The circuit chamber 235 is disposed on the upstream side in the flow direction of the measured gas 2 in the main passage 22, and the sub-passage 234 is located on the downstream side in the flow direction of the measured gas 2 in the main passage 22 with respect to the circuit chamber 235. The circuit board 207 is disposed in substantially parallel to the measured gas 2 flowing in the main passage 22. Consequently, the sizes in a longitudinal direction and a thickness direction of the measuring unit 213 can be reduced, and a physical quantity detection device having a low pressure loss can be proposed. In particular, when the detection functions of the intake air temperature sensor 203, the humidity sensor 206, the pressure sensor 204, and the like are made multifunctional, it is more effective because the size of the circuit board 207 increases due to a control circuit, a protection circuit, the number of circuit wirings, and addition of an electronic component.

A chip package 208 including the flow sensor 205 that measures the flow rate of the measured gas 2 flowing in the main passage 124 is accommodated in the housing 201 while being mounted on a circuit board 207 on which a plurality of sensors can be mounted. FIG. 6A illustrates an example in which a pressure sensor 204, a humidity sensor 206, and the intake air temperature sensor 203 are mounted in addition to the chip package 208. However, it is not necessary to mount all the sensors depending on the requirements, so that the necessary sensors may be mounted according to the requirements. The circuit board 207 forms a mounting portion corresponding to all sensors, and can be commonly used with respect to a sensor mounting pattern for each requirement.

The chip package 208 is fixed to a circuit board surface of the circuit board 207 with a part of the chip package 208 projecting laterally from the end of the circuit board 207. The chip package 208 is disposed between the sub-passage 234 and the circuit chamber 235.

Consequently, the circuit chamber 235 and the sub-passage 234 are separated, and the flow to the flow sensor 205 disposed in the chip package 208 can be controlled by the shape of the sub-passage 234. For this reason, there is no barrier that obstructs the flow in the sub-passage 234, and a stable flow can be supplied to the flow sensor 205. Thus, the downsizing of the measuring unit 213 can be achieved while the flow speed sensitivity, noise performance, and pulsation characteristics of the flow sensor are maintained.

The space saving can be achieved when the wall on the upstream side of the circuit chamber 235 is used as the side face 223 on one side.

In the embodiment, the flow sensor 205 is disposed in the chip package 208 and mounted on the circuit board 207. Alternatively, the flow sensor 205 may be mounted with another support other than the chip package 208 interposed therebetween. The circuit board 207 is formed so as to protrude partially, whereby the circuit board 207 itself may have a support function.

The sub-passage groove 250 forms the sub-passage 234 in conjunction with the cover 202. The sub-passage 234 extends along the protruding direction (longitudinal direction) of the measuring unit. The sub-passage groove 250 forming the sub-passage 234 includes a first sub-passage groove 251 and a second sub-passage groove 252 branched in the middle of the first sub-passage groove 251. The first sub-passage groove 251 is formed so as to extend along the short-side direction of the measuring unit 213 between the inlet 231 open to the step surface 228 of the measuring unit 213 and the first outlet 232 open to the side face on the other side of the measuring unit 213 and at the position opposed to the step surface 228. The inlet 231 is disposed toward the upstream side in the flow direction of the measured gas 2 in the main passage 22. The first sub-passage groove 251 constitutes a first sub-passage that takes in the measured gas 2 flowing in the main passage 22 from the inlet 231 and returns the taken measured gas 2 from the first outlet 232 to the main passage 22. The first sub-passage extends from the inlet 231 along the flow direction of the measured gas 2 in the main passage 22, and is connected to the first outlet 232.

The second sub-passage groove 252 branches in the middle of the first sub-passage groove 251 and extends toward the base end side (flange side) of the measuring unit 213 along the longitudinal direction of the measuring unit 213. Then, the second sub-passage groove 252 is bent toward the other side in the short-side direction of the measuring unit 213 at the base end of the measuring unit 213, and returned to extend again toward the leading edge end of the measuring unit 213 along the longitudinal direction of the measuring unit 213. Then, the second sub-passage groove 252 is provided so as to be bent toward the other side in the short-side direction of the measuring unit 213 in front of the first outlet 232 to continue to the second outlet 233 open to the side face 224 on the other side of the measuring unit 213. The second outlet 233 is disposed toward the downstream side in the flow direction of the measured gas 2 in the main passage 22. The second outlet 233 has an opening area that is substantially the same as or slightly larger than that of the first outlet 232, and is formed at a position adjacent to the base end side in the longitudinal direction of the measuring unit 213 with respect to the first outlet 232.

The second sub-passage groove 252 constitutes a second sub-passage that allows the measured gas 2 branched and flowing from the first sub-passage to pass, and returns the measured gas 2 from the second outlet 233 to the main passage 22. The second sub-passage includes a path that reciprocates along the longitudinal direction of the measuring unit 213.

That is, the second sub-passage includes the path that branches in the middle of the first sub-passage, extends toward the base end side of the measuring unit 213, is folded back on the base end side of the measuring unit 213, extends toward the leading edge side of the measuring unit 213, and continues to the second outlet 233 disposed toward the downstream side in the flow direction of the measured gas 2 on the downstream side in the flow direction of the measured gas 2 in the main passage 22 with respect to the inlet 231. In the second sub-passage groove 252, a flow sensor 205 is disposed at a midway position. The second sub-passage groove 252 can secure a longer passage length of the second sub-passage, and decrease the influence on the flow sensor 205 when pulsation is generated in the main passage.

With the above configuration, the sub-passage 234 can be formed along the direction in which the measuring unit 213 extends, and the length of the sub-passage 234 can be secured sufficiently long. Consequently, the physical quantity detection device 20 can include the sufficiently long sub-passage 234. Thus, the physical quantity detection device 20 can measure the physical quantity of the measured gas 30 with high accuracy while suppressing the fluid resistance to a small value.

Because the first sub-passage groove 251 extends from the inlet 231 to the first outlet 232 along the short-side direction of the measuring unit 213, a foreign matter such as dust invading into the first sub-passage from the inlet 231 can be discharged as it is from the first outlet 232, and the foreign matter can be prevented from invading into the second sub-passage, and prevented from affecting the flow sensor 205 in the second sub-passage.

In the inlet 231 and the first outlet 232 of the first sub-passage groove 251, the inlet 231 is larger than the first outlet 232 in the opening area. When the opening area of the inlet 231 is enlarged larger than that of the first outlet 232, the measured gas 2 flowing into the first sub-passage can certainly be led to the second sub-passage branching in the middle of the first sub-passage.

A protrusion 253 is provided at the center in the longitudinal direction of the inlet 231 of the first sub-passage groove 251. In the protrusion 253, the size of the inlet 231 is equally divided into two in the longitudinal direction, and the opening areas of each divided inlet 231 is smaller than that of the first outlet 232 and the second outlet 233. The protrusion 253 can prevent the foreign matter from blocking the first outlet 232 and the second outlet 233 by restricting the size of the foreign matter that can invade into the first sub-passage from the inlet 231 to be smaller than the sizes of the first outlet 232 and the second outlet 233.

<Arrangement Position of Each Sensor>

As illustrated in FIG. 6A, the circuit chamber 235 is provided on one side in the short-side direction of the measuring unit 213, and accommodates the circuit board 207. The circuit board 207 has a rectangular shape extending along the longitudinal direction of the measuring unit, and the chip package 208, the pressure sensor 204, and the humidity sensor 206 are mounted on the surface of the circuit board 207.

The chip package 208 is mounted on the circuit board 207. In the chip package 208, the flow sensor 205 and an LSI that is an electronic component that drives the flow sensor 205 are sealed by transfer molding. The flow sensor 205 and the LSI may be integrally formed in the same semiconductor element, or formed as separate semiconductor elements. The resin is sealed such that at least the flow rate measuring unit of the flow sensor 205 is exposed. The structure in which the LSI is provided in the chip package 208 is described by way of example. Alternatively, a structure in which the LSI is mounted on the circuit board 207 may be used. An advantage of providing the LSI in the chip package 208 is that it is not necessary to mount the LSI on the circuit board 207, which contributes to the downsizing of the circuit board 207.

The chip package 208 has a shape that is gradually narrowed from the edge of the side face to the flow sensor 205. This narrowed shape rectifies the fluid flowing through the sub-passage, and reduces the influence of the noise. Preferably the narrowed shape can increase the speed of the fluid when not only the chip package is narrowed in a direction of a paper surface (the surface direction of the chip package) but also the chip package is narrowed by inclining the chip package in a vertical direction of the paper surface (the thickness direction of the chip package). An advantage of the chip package 208 is that the narrowed shape can accurately be formed with respect to the flow sensor 205 because the narrowed shape is formed integrally with the flow sensor 205. Although a dimensional accuracy error becomes severe with the downsizing, the narrowing can accurately be formed, so that the flow rate detection accuracy can be improved.

The chip package 208 is mounted with a part of the chip package 208 protruding from the circuit board 207 onto the other side in the short-side direction at the center position in the longitudinal direction of the circuit board 207 such that the flow sensor 205 is disposed in the second sub-passage groove 252.

More preferably, the leading edge side of the circuit package is disposed in the sub-passage such that the fluid flows on both the front face side that is the measuring unit side and the back face side thereof. This is because the amount of dust reaching the front face side on which the measuring unit is formed can be decreased by causing also the fluid to flow on the back face side.

The pressure sensor 204 is mounted on the base end side in the longitudinal direction of the circuit board 207 with respect to the chip package 208, and the humidity sensor 206 is mounted on the leading edge side in the longitudinal direction of the circuit board 207 with respect to the chip package 208. A lead of the intake air temperature sensor 203 is connected to the surface of the circuit board 207. The intake air temperature sensor 203 is mounted such that the lead 203b is connected to the position on the leading edge side in the longitudinal direction of the circuit board 207 with respect to the humidity sensor 206, and such that the sensor body 203a is disposed at the position where the sensor body 203a protrudes from the circuit board 207 in the longitudinal direction and is exposed to the outside of the measuring unit 213.

In the measuring unit 213, (1) the pressure sensor 204, (2) the flow sensor 205, (3) the humidity sensor 206 and (4) the intake air temperature sensor 203 are disposed in order from the base end side toward the leading edge side along the longitudinal direction (toward the protruding direction of the measuring unit 213). In other words, the pressure sensor 204, the flow sensor 205, the humidity sensor 206, and the intake air temperature sensor 203 are disposed on the circuit board 207 in order from the flange side.

(1) The pressure sensor 204 detects the pressure of the measured gas 2, and the flow sensor 205 detects the flow rate of the measured gas 2. The humidity sensor 206 detects humidity of the measured gas 2, and the intake air temperature sensor detects a temperature of the measured gas 2.

FIG. 7A illustrates an example of a numerical graph indicating a temperature influence range that is allowed to ensure the measurement accuracy of each sensor. The graph ranges from −25° C. (that is, 0° C.) to +50° C. (that is, 75° C.) with respect to a reference temperature of 25° C.

In the numerical graph in FIG. 7A, (1) the pressure sensor 204 has a temperature influence allowable range between −25° C. and 50° C., the widest temperature influence allowable range among the sensors, and a small thermal influence. (2) The flow sensor 205 has a wide temperature influence allowable range on the high temperature side and the small thermal influence on the high temperature side. On the other hand, (3) the humidity sensor 206 has the wide temperature influence allowable range on the low temperature side and the small thermal influence on the low temperature side. (4) The intake air temperature sensor 203 has the temperature influence allowable range only in the vicinity including the reference temperature of 25° C., the narrowest temperature influence allowable range among the sensors, and the large thermal influence.

The difference of the temperature influence allowable range in FIG. 7A depends greatly on a detection principle of each sensor. For example, in the pressure sensor having the widest temperature influence allowable range, a semiconductor type pressure sensor is typically used, a strain gauge is formed on a surface of a diaphragm, and a change in electric resistance by a piezoresistance effect generated by deformation of the diaphragm due to external pressure is converted into an electric signal. The measurement error due to the temperature influence depends mainly on temperature dependence of a piezoresistor, and the temperature dependence of the piezoresistor has relatively good linearity, and the measurement error can be prevented by temperature compensation. On the other hand, for the temperature sensor having the narrowest temperature influence allowable range, the temperature is measured by heat transfer with the measured gas 2, and a temperature error is directly generated when the thermal influence from a heat conducting member such as a substrate is generated. For this reason, the allowable range is basically narrowed.

For example, the physical quantity detection device 20 is disposed in an engine room of an automobile.

The temperature in the engine room ranges from 60° C. to 100° C., and the temperature of the measured gas 2 passing through the main passage 22 is 25° C. on average. Thus, the heat in the engine room is transmitted from the side of the flange 211 to the physical quantity detection device 20, and the temperature is gradually lowered from the side of the flange 211 toward the leading edge side of the measuring unit 213 in a temperature distribution.

Figure 7B:
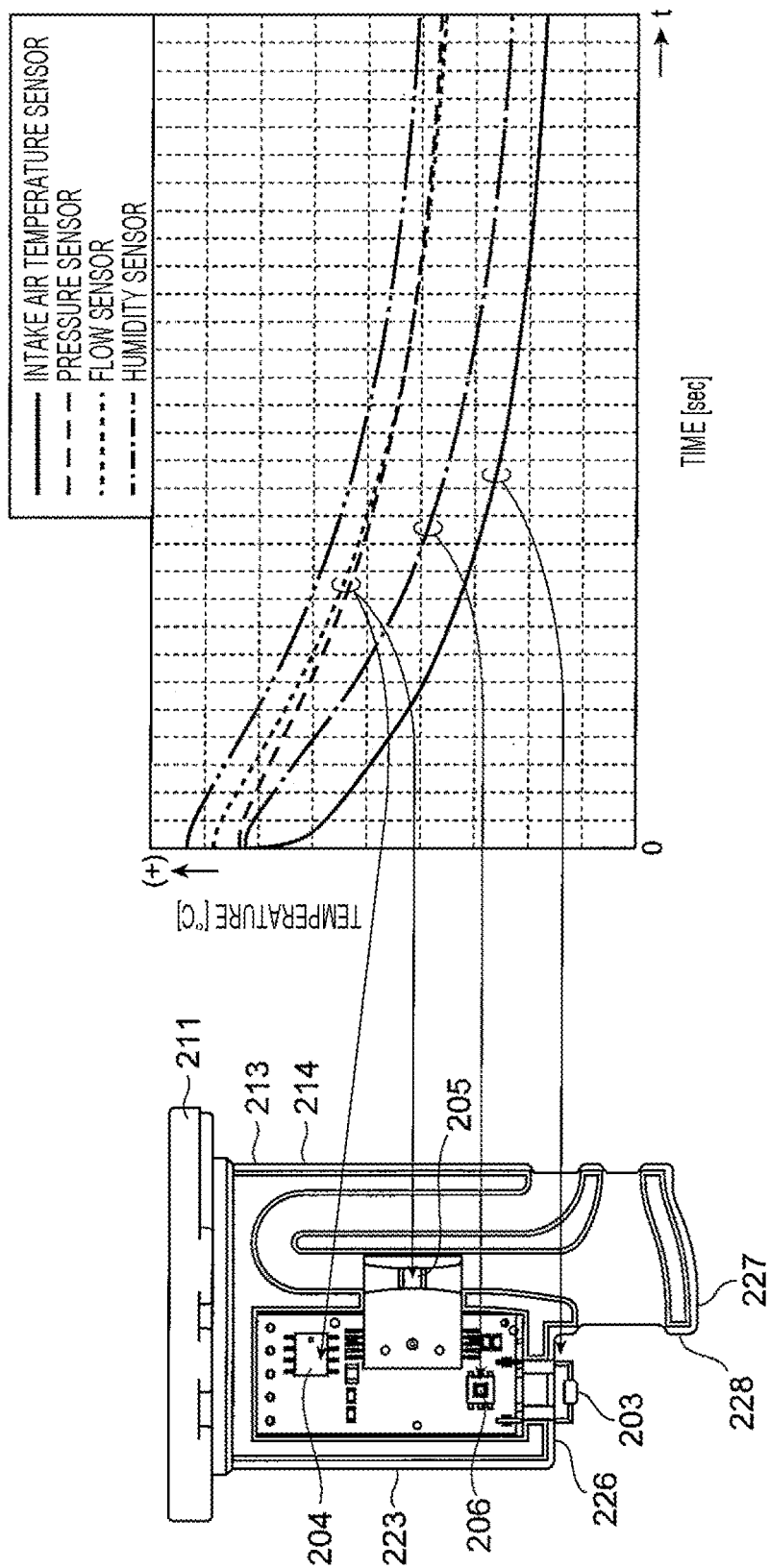
FIG. 7B is a graph illustrating a temperature change of each sensor in an engine room.

Thus, in the measuring unit 213 of the embodiment, (1) the pressure sensor 204 having the smallest thermal influence is disposed on the base end side that is the flange side, and then (2) the flow sensor 205 is disposed on the leading edge side of the measuring unit 213 with respect to (1) the pressure sensor 204. Next, the thermal effect is the smallest on the low temperature side. (3) The humidity sensor 206 having the small thermal influence on the low temperature side is displaced on the leading edge side of the measuring unit 213 with respect to (2) the flow sensor 205, and is most susceptible to thermal effects. (4) The intake air temperature sensor 203 that is most susceptible to thermal influence is disposed at the leading end of the measuring unit 213. FIG. 7B is a graph illustrating a temperature change of each sensor in the engine room. A temperature distribution corresponding to the arrangement order of each sensor is obtained as illustrated in FIG. 7B.

According to the embodiment, the circuit board 207 is arranged so as to extend along the longitudinal direction of the measuring unit 213, so that the heat conduction distance from the flange 211 can be ensured to the vicinity of the center axis of the main passage 22. Each of the sensors (1) to (4) is arranged in order from the base end of the measuring unit 213 toward the leading edge in the ascending order of the thermal influence, so that the sensor performance of each sensor can be ensured even if the mounting space is restricted due to the downsizing. The heat transfer to the air can be promoted by disposing the circuit board 207 on one side in the short-side direction of the measuring unit 213.

<Sealing Structure in Circuit Chamber>

Figure 8A:
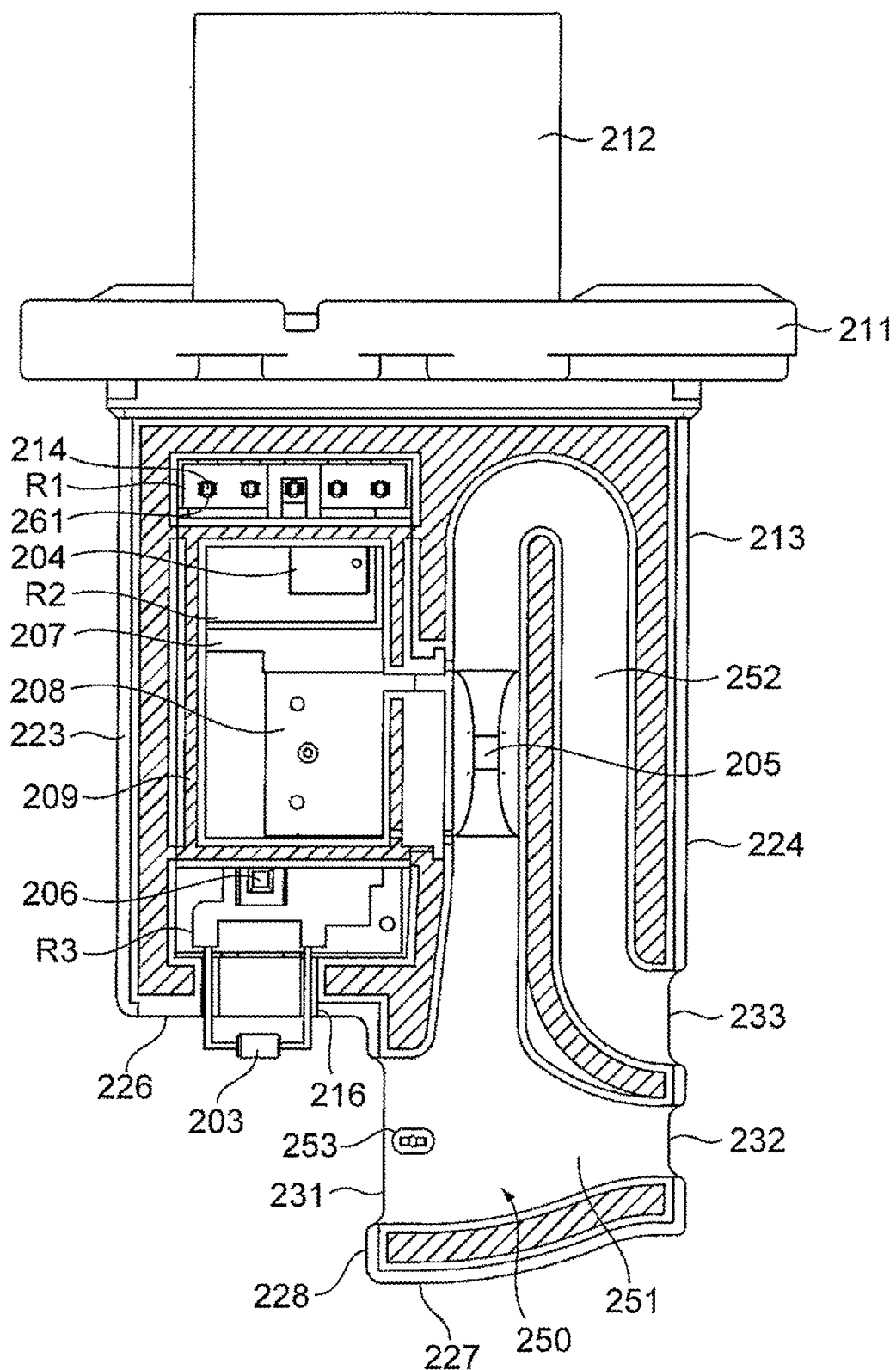
FIG. 8A is a front view of the housing with the cover removed.
Figure 8B:
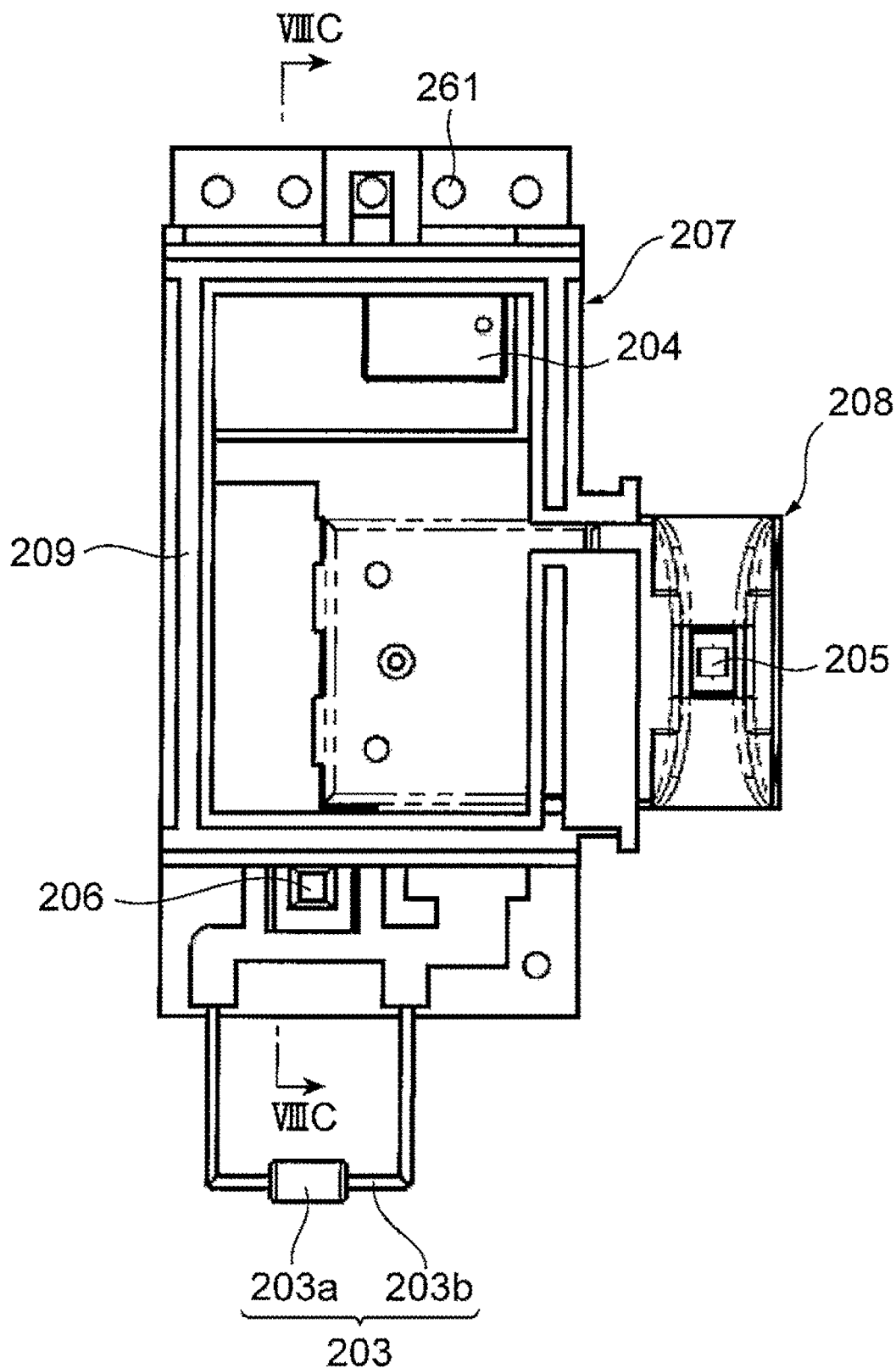
FIG. 8B is a front view of a circuit board.
Figure 8C:
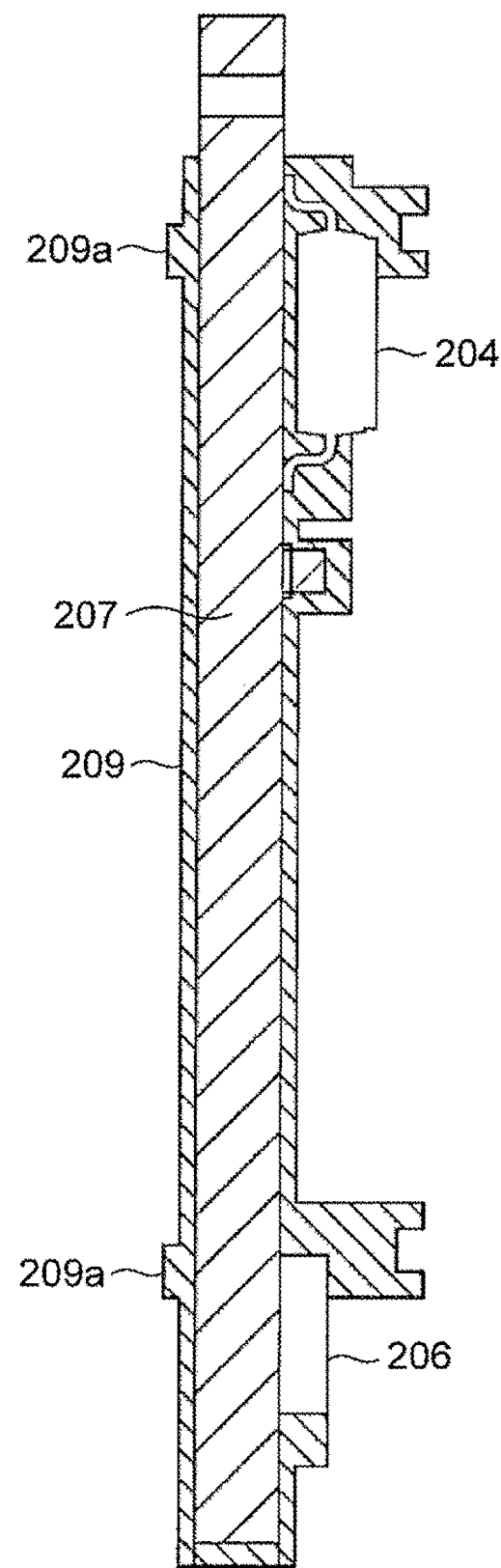
FIG. 8C is a sectional view taken along line a VIIIC-VIIIC in FIG. 8B.

FIG. 8A is a front view of the housing with the cover removed, FIG. 8B is a front view of the circuit board 207, and FIG. 8C is a sectional view taken along a line VIIIC-VIIIC in FIG. 8B.

As illustrated in FIGS. 8A to 8E, the circuit board 207 is coated with a hot-melt adhesive 209 to protect the conductive portion between the circuit board 207 and each sensor. A sensor surface of each sensor is exposed without being covered with the hot-melt adhesive 209, and the sensing function is not lost. For example, the hot-melt adhesive 209 is made of a thermoplastic resin material having an elastically deformable property, and is applied to the circuit board 207 in a heat-softened state.

In the circuit chamber, the hatched portion in FIG. 8A adheres to the cover by an adhesive, and the front face side of the circuit board 207 is hermetically partitioned into three chambers R1, R2, R3 by the adhesive and the hot-melt adhesive 209. Specifically, the first chamber R1 in which a connector terminal 214 molded integrally with the housing 201 and the connection terminal of the circuit board 207 are connected, the second chamber R2 in which the pressure sensor 204 and a part of the chip package 208 are accommodated, and the third chamber R3 in which the humidity sensor 206 is accommodated and the lead 203b of the intake air temperature sensor 203 is inserted are formed.

The first chamber R1 is sealed by the cover 202 on the front face side, and constitutes a sealed space isolated from the outside of the measuring unit 213. Thus, the connection portion between the connector terminal 214 and the connection terminal can be prevented from corroding due to contact with a gas contained in the measured gas 2.

The second chamber R2 communicates with the second sub-passage 252 through a gap with the cover 202, and the pressure of the second chamber R2 can be measured by the pressure sensor 204. A ventilation hole 274 of the ventilation passage formed in the chip package 208 to prevent the sealing of the back face of the diaphragm of the flow sensor 205 is disposed, so that the back face of the diaphragm can be maintained in an open state.

The third chamber R3 communicates with the outside of the measuring unit 213 through an intake air temperature sensor lead insertion hole 216 open to the bottom surface 226 of the measuring unit 213, and humidity can be measured by the humidity sensor 206. The lead insertion hole 216 serving as a communication path through which a measurement medium is led to the humidity sensor 206 is made at a position where the fluid is separated by the side face 223 on one side, so that the entry of water droplets and dust that are contaminated materials. A measurement target can be led to the measuring unit 213 while a water droplet and dust that are contaminated materials can be prevented from invading.

The structure partitioning the second chamber R2 and the third chamber R3 is illustrated. Alternatively, the same space may be used without partitioning the second chamber R2 and the third chamber R3.

<Structure of Single Housing>

Figure 9A:
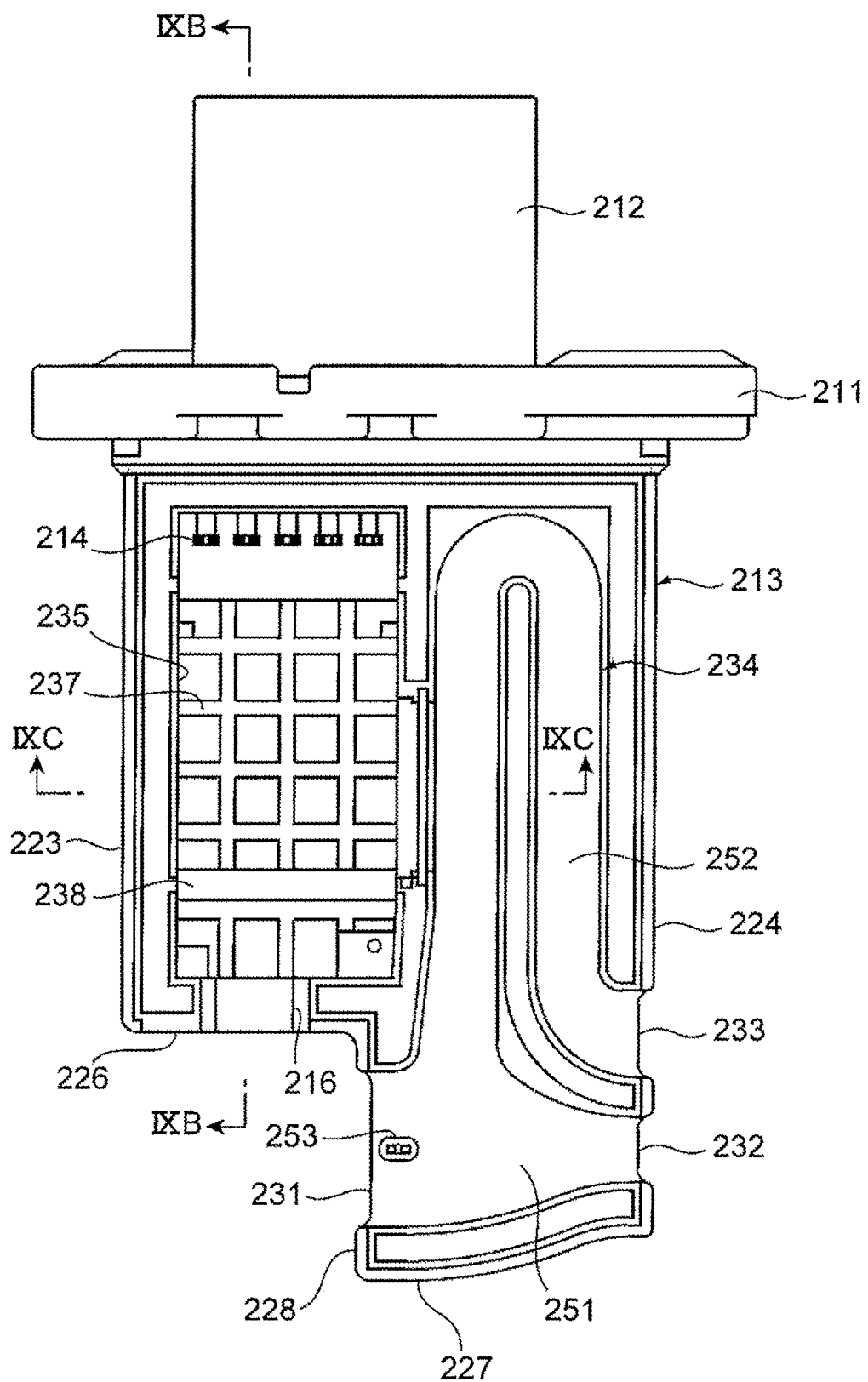
FIG. 9A is a front view of the housing with the cover and the circuit board removed.
Figure 9B:
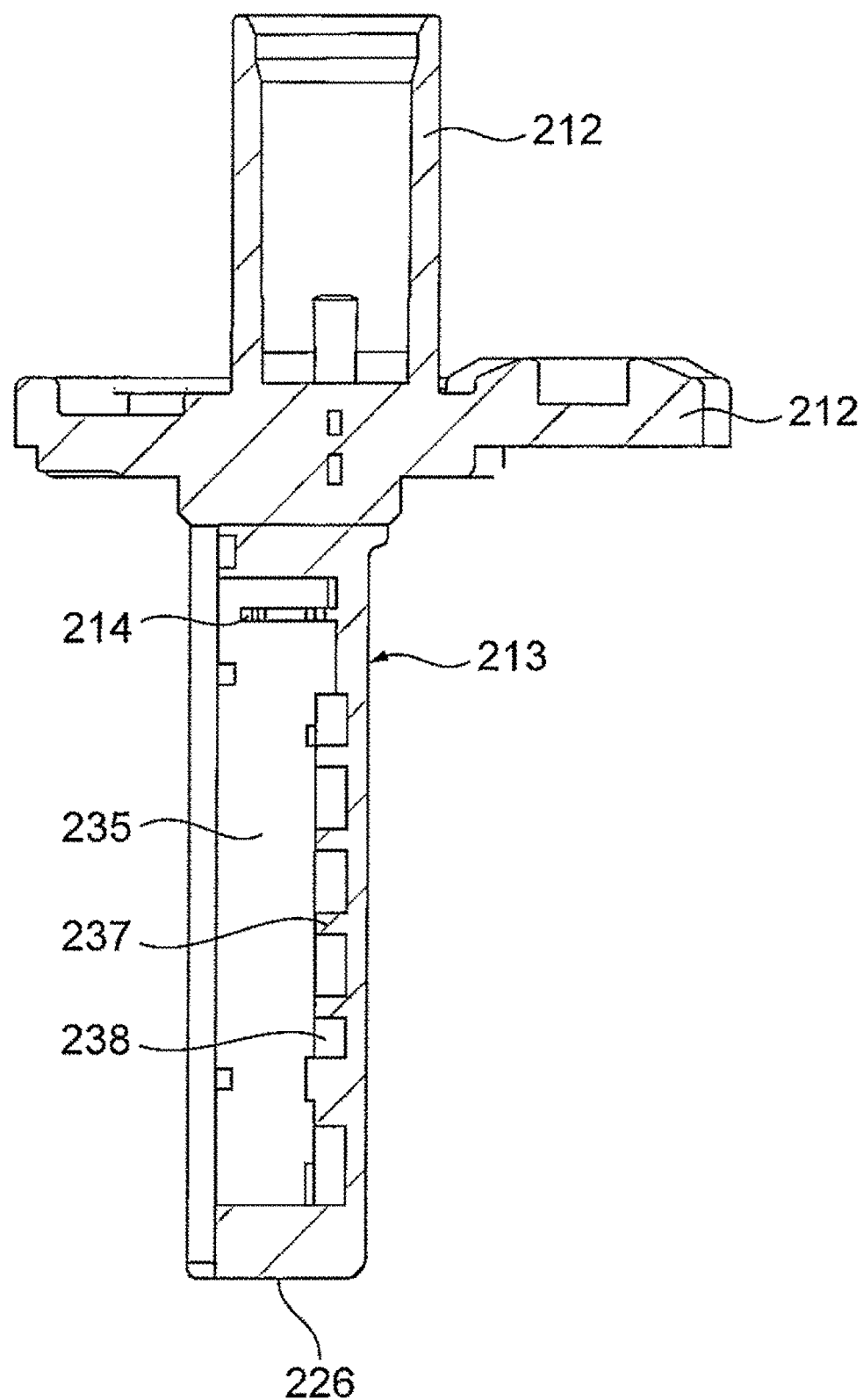
FIG. 9B is a sectional view taken along a line IXB-IXB in FIG. 9A.
Figure 9C:
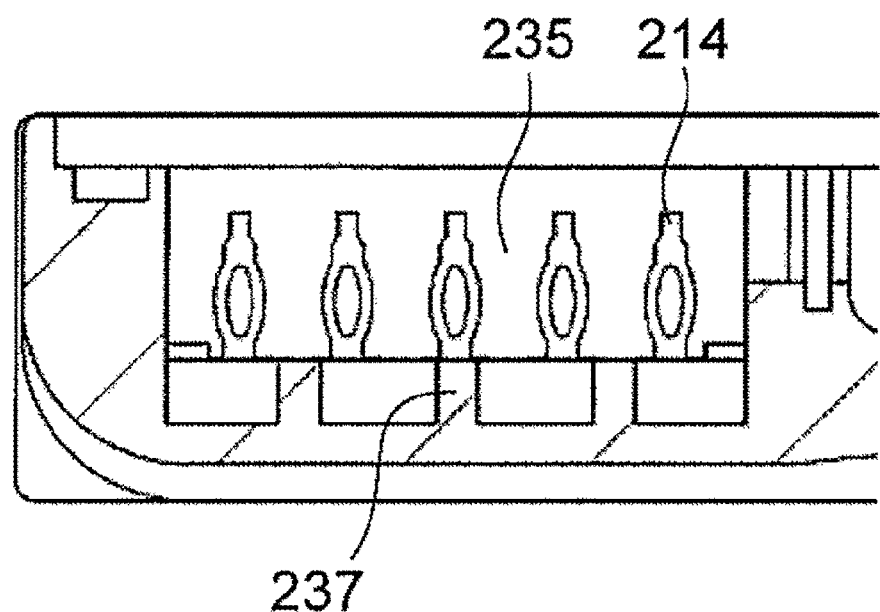
FIG. 9C is a sectional view taken along a line IXC-IXC in FIG. 9A.

FIG. 9A is a front view of the housing with the cover and the circuit board removed, FIG. 9B is a sectional view taken along a line IXB-IXB in FIG. 9A, and FIG. 9C is a sectional view taken along a line IXC-IXC in FIG. 9A.

In the housing 201, as illustrated in FIG. 9A, a rib 237 is provided in the bottom surface of the circuit chamber 235. The rib 237 includes a plurality of vertical ribs extending along the longitudinal direction of the measuring unit and a plurality of horizontal ribs extending along the short-side direction of the measuring unit 213, and is provided in a lattice shape.

The housing 201 can obtain high rigidity without increasing the thickness by providing the rib 237 in the measuring unit 213. In the housing 201, the flange 211 and the measuring unit 213 are largely different from each other in the thickness, and the difference in the heat shrinkage rate after injection molding is large, so that the measuring unit 213 having a smaller thickness than the flange 211 is easy to deform. Thus, a distortion of the measuring unit 213 can be prevented during heat shrinkage by providing the lattice-shaped ribs 237 spreading in a planar shape on the bottom surface of the circuit chamber 235.

In the housing 201, the rib 237 is provided on not the outer wall of the measuring unit 213, but the bottom surface (inside the housing) of the circuit chamber 235. When the rib 237 is provided on the outer wall of the measuring unit 213, there is a risk of affecting the flow of the measured gas 2 passing through the main passage 22. For example, in the case where a depth of the circuit chamber 235 is set on the assumption that the single-side mounting circuit board 207 is accommodated, it is necessary to increase the depth of the circuit chamber 235 when the specifications is changed to accommodate the double-side mounting circuit board 207. On the other hand, when the rib is provided on the outer wall of the measuring unit 213, the rib protrudes by the amount of the increased depth of the circuit chamber 235, and the thickness of the measuring unit 213 is increased. Thus, the single-side mounting and the double-side mounting are different from each other in the thickness of the measuring unit 213, and there is a risk of affecting the detection accuracy.

On the other hand, in the embodiment, because the rib 237 is provided on the bottom surface of the circuit chamber 235, the flow of the measured gas 2 passing through the main passage 22 is prevented from being affected, and the measured gas 2 can be caused to flow smoothly. The depth of the bottom surface of the circuit chamber 235 can be changed only by changing a height of the ribs 237 in the circuit chamber 235, and it is not necessary to change the thickness of the measuring unit regardless of whether the circuit board 207 is either the single-side mounting or the double-side mounting.

A connector terminal 214 is formed integrally with the housing 201. The base end of the connector terminal 214 is connected to an external terminal in the connector 212 and a leading edge of the connector terminal 214 is provided while protruding into the circuit chamber 235. As illustrated in FIG. 9C, the connector terminal 214 includes a terminal (needle eye) in which the leading edge can elastically be deformed in the width direction, and has a press-fit structure in which the end of the connector terminal 214 is press-fitted in the through-hole 261 of circuit board 207 to establish electric connection by disposing the circuit board 207 in the circuit chamber 235.

A groove hole 238 is made in the bottom surface of the circuit chamber 235 to position and support the circuit board 207. In the circuit board 207, a protrusion 209a provided at a corresponding position. The protrusion 209a is formed by projecting a part of the hot-melt adhesive 209. The protrusion 209a formed of the hot-melt adhesive 209 having the elastically deformable property is fitted in the groove hole 238, whereby the circuit board 207 is supported in the circuit chamber 235 while the vibration transmission from the housing 201 is prevented.

<Structure of Cover>

For example, the cover 202 is made of a metal conductive material such as an aluminum alloy or a stainless alloy or a conductive material such as a conductive resin. The cover 202 has a flat plate shape covering the front face of the measuring unit 213, and is fixed to the measuring unit 213 using an adhesive. The cover 202 covers the circuit chamber 235 of the measuring unit 213, and constitutes the sub-passage in conjunction with the sub-passage groove 250 of the measuring unit 213. The cover 202 is electrically connected to the ground by interposing a conductive intermediate member between the cover 202 and the circuit board 207 or the connector terminal 214, whereby the wall surface of the sub-passage has a charge eliminating function. The electrification of the charged particles is removed to prevent the contamination from adhering to the flow sensor 205.

A conductive rubber, a conductive adhesive, a silver paste, or solder is used as the intermediate member. The charge eliminating function can be achieved with no use of the intermediate member by directly bringing the cover 202 into contact with the circuit board or the connector terminal 214. In this case, the cover may be made of a conductive resin in order to prevent the generation of cutting waste due to the vibration.

<Structure of Circuit Board 207>

Figure 10A:
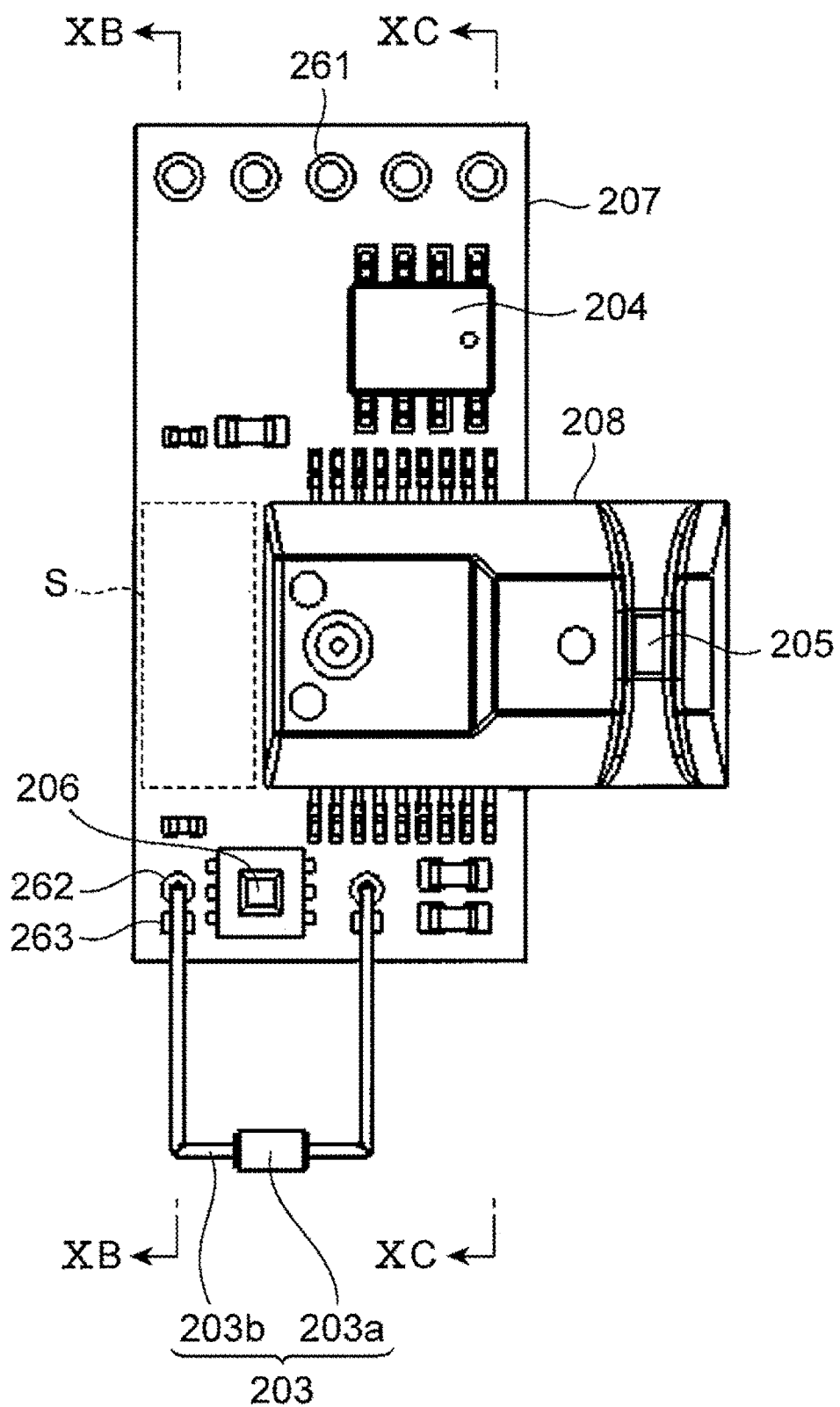
FIG. 10A is a front view of the circuit board on which a chip package and a circuit component are mounted.
Figure 10B:
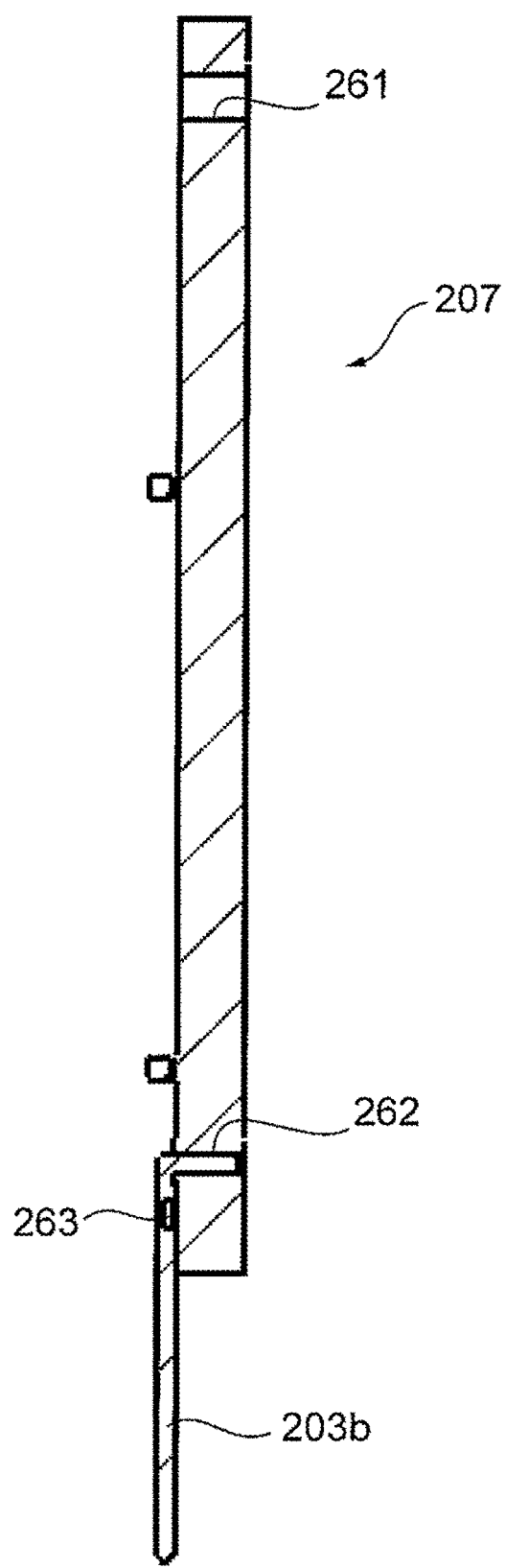
FIG. 10B is a sectional view taken along a line XB-XB in FIG. 10A.
Figure 10C:
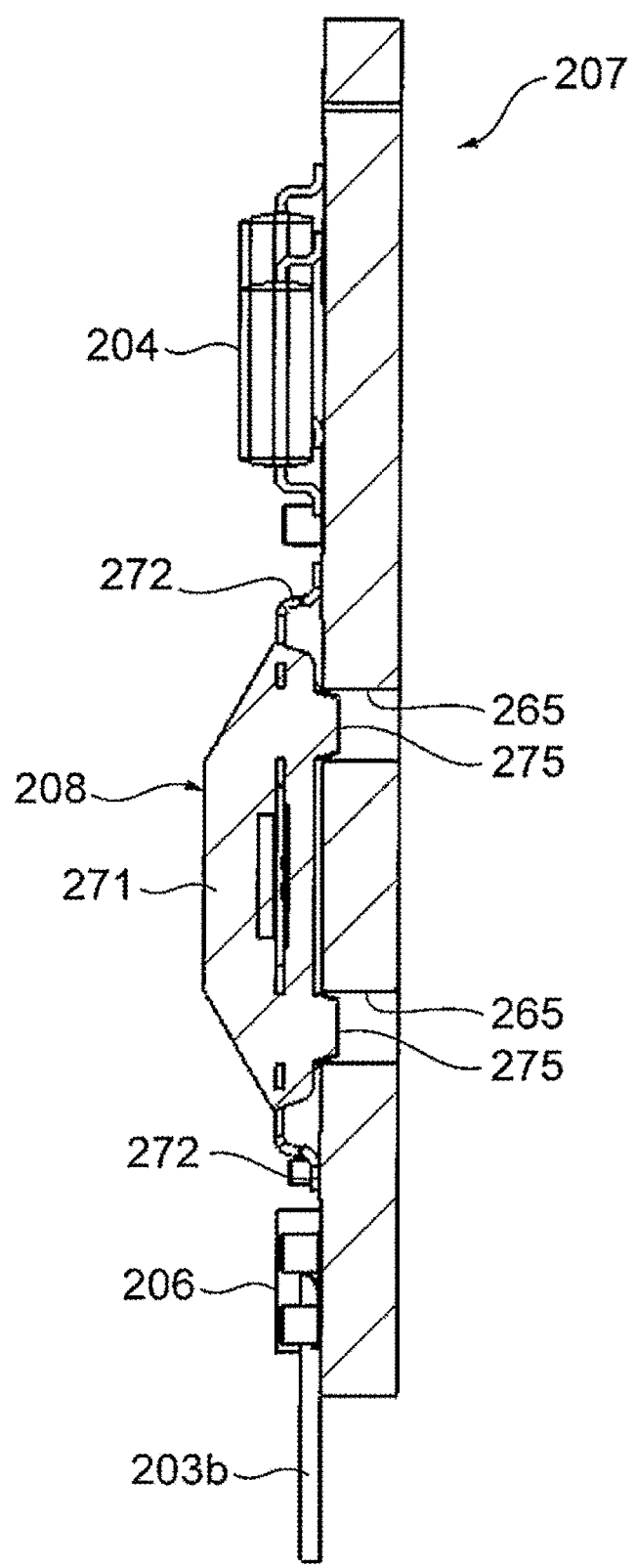
FIG. 10C is a sectional view taken along a line XC-XC in FIG. 10A.
Figure 11A:
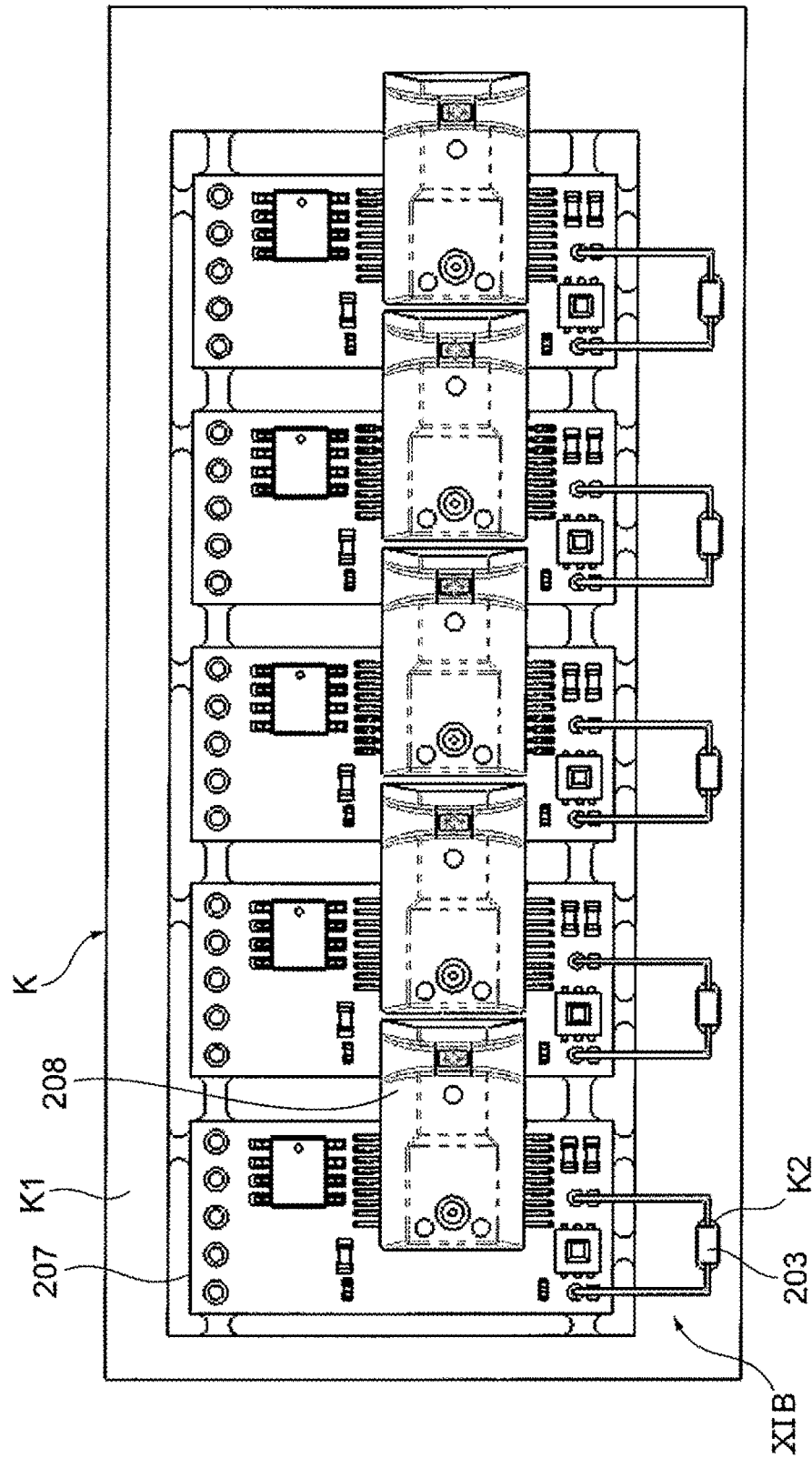
FIG. 11A is a view illustrating a board sheet on which a plurality of circuit boards in FIG. 10A are formed.
Figure 11B:
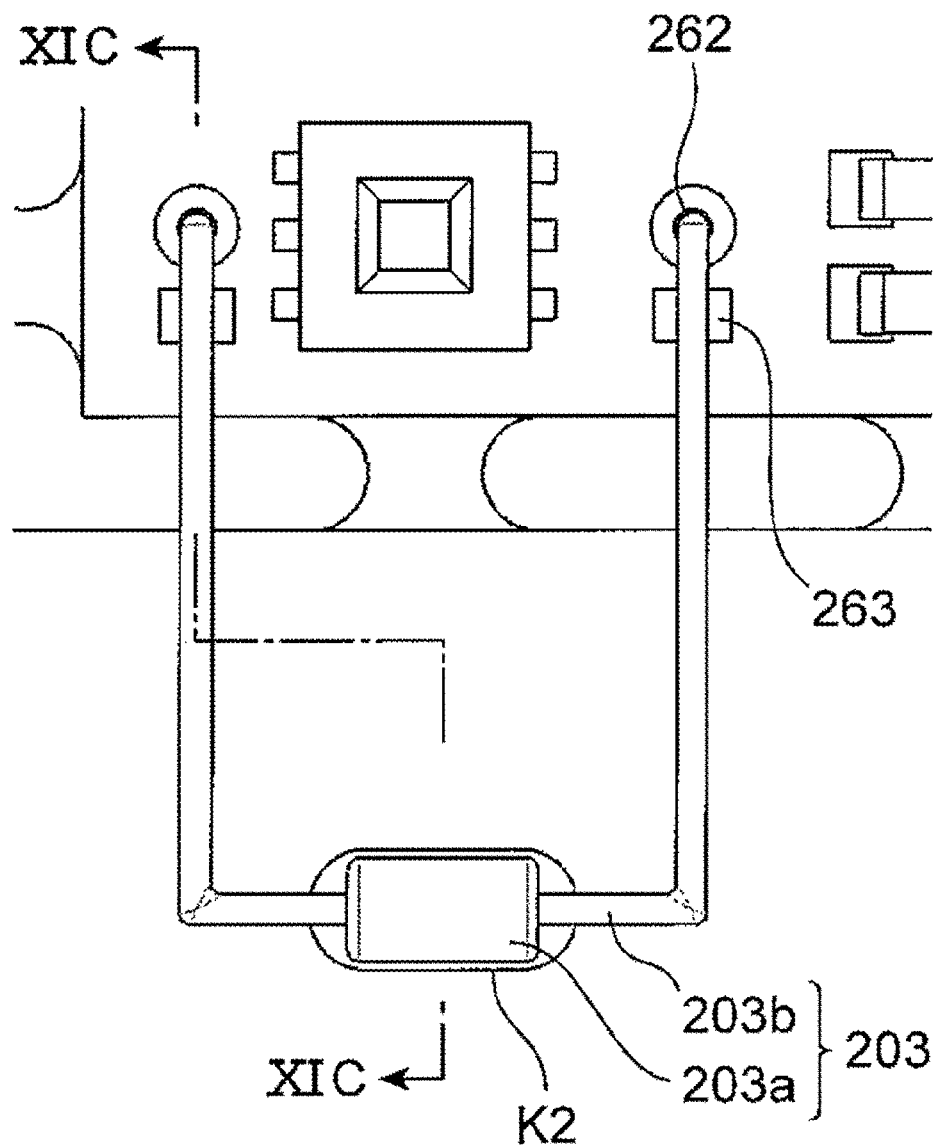
FIG. 11B is an enlarged view illustrating a XIB portion in FIG. 11A.
Figure 11C:
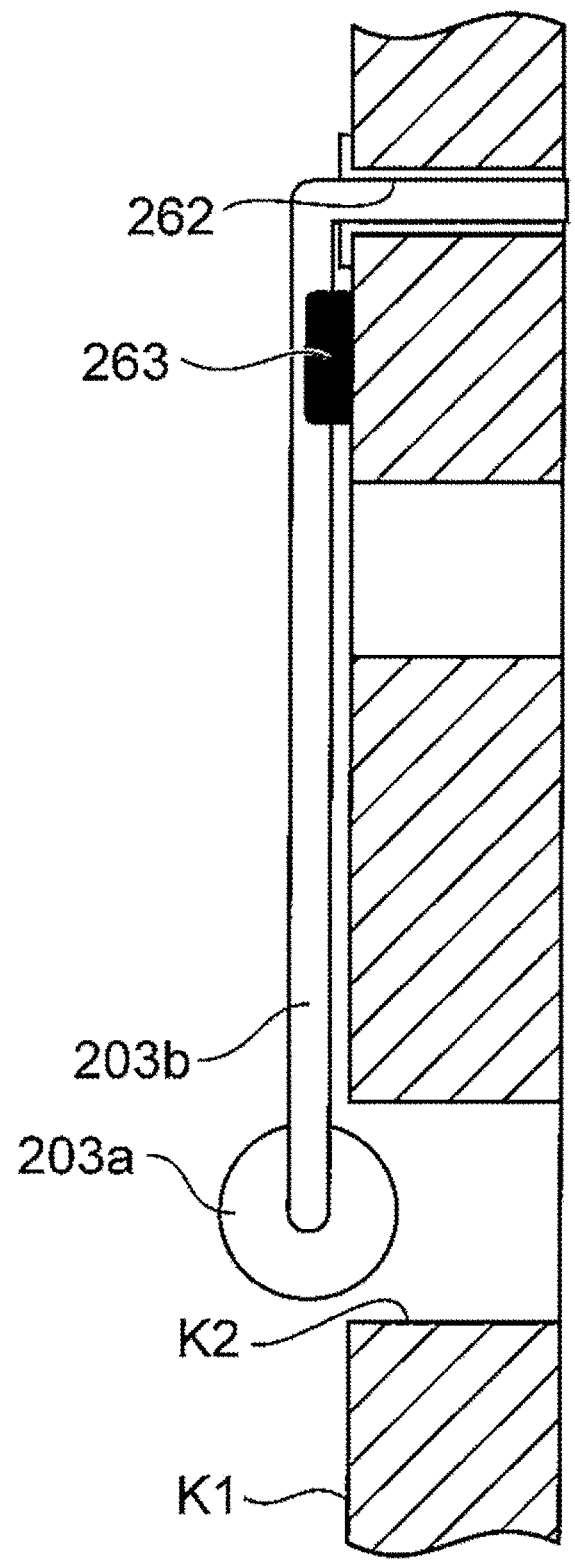
FIG. 11C is a sectional view taken along a line XIC-XIC in FIG. 11B.

FIG. 10A is a front view of the circuit board on which the chip package and circuit components are mounted, FIG. 10B is a sectional view taken along a line XB-XB in FIG. 10A, and FIG. 10C is a sectional view taken along a line XC-XC in FIG. 10A. FIG. 11A is a view illustrating a substrate sheet on which a plurality of circuit boards in FIG. 10A are formed, FIG. 11B is an enlarged view of a XIB portion in FIG. 11A, FIG. 11C is a sectional view taken along a line XIC-XIC in FIG. 11B, and FIG. is a view illustrating the substrate sheet on which a plurality of circuit boards of comparative examples are formed.

The circuit board 207 has a rectangular shape (a shape in which an aspect ratio of the vertical and horizontal dimensions is larger than 1) extending along the longitudinal direction of the measuring unit 213. The through-hole 261 in which the connector terminal 214 of the housing 201 is press-fitted is provided at one end in the longitudinal direction of the circuit board 207. A mounting location for the pressure sensor 204 is provided adjacent to the through-hole 261. One pressure sensor 204 may be provided as illustrated in FIG. 10A, or a plurality of pressure sensors 204 may be arranged side by side.

The chip package 208 is fixed at the center position in the longitudinal direction of the circuit board 207. The chip package 208 is mounted such that a part of the chip package 208 protrudes from the end of the circuit board 207. Specifically, the base end of the chip package 208 is fixed at the center position in the longitudinal direction of the circuit board 207 and at the position biased to one side in the short-side direction, and the leading edge of the chip package 208 is disposed at the position protruding from the circuit board 207 along the short-side direction. The flow sensor 205 is provided at the leading edge of the chip package 208, and disposed in the second sub-passage groove 252. The circuit board 207 includes a margin region S greater than or equal to the width of the chip package 208 at the position on the circuit board surface of the circuit board 207 and at the position biased in the opposite direction to the protruding direction of the chip package 208 with respect to the chip package 208. The margin region S is provided on the other side in the short-side direction of the chip package 208. In the margin region S, the circuit board is not disposed, and the circuit board surface is exposed. The margin region S is a region where the circuit component is not mounted thereon although the circuit wiring is included.

Figure 12:
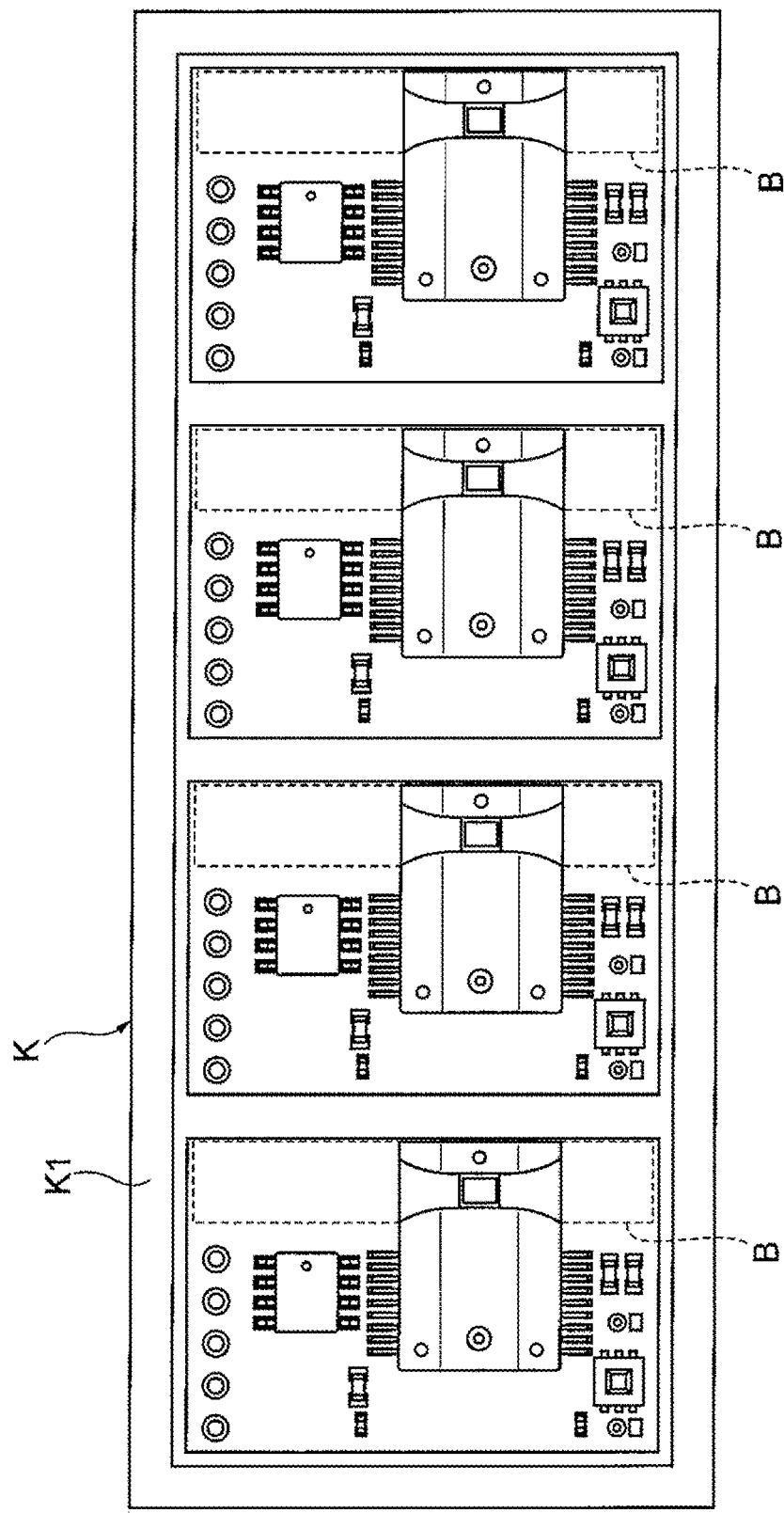
FIG. 12 is a view illustrating the board sheet on which a plurality of circuit boards of a comparative example are formed.

In the embodiment, as illustrated in FIG. 11A, when the chip package 208 is mounted on the circuit board 207 while protruding from the circuit board 207, the size of the circuit board 207 can be reduced as compared with the case where the whole chip package 208 is accommodated on the surface of the circuit board 207 like the comparative example illustrated in FIG. 12. For the comparative example in FIG. 12, because a portion surrounded by a broken line B in the circuit board 207 is disposed in the sub-passage, the component cannot be mounted, and the portion becomes a wasted space.

On the other hand, in the circuit board 207 of the embodiment, the size of about 30% can be omitted from the comparative example by the protruding mounting, and the downsizing of the circuit board 207 can be achieved.

Because the margin region S is provided in the region on the other side in the short-side direction with respect to the chip package 208 of the circuit board 207, the leading edge of the chip package 208 protruding from the circuit board 207 can be mounted on the margin region S of another adjacent circuit board 207 when the chip package 208 is mounted on each circuit board 207 on a board sheet K as illustrated in FIG. 11A. That is, the margin region S has a size that can place the protruding portion of the chip package mounted on another adjacent circuit board when the chip package 208 is mounted on the circuit board 207 in the state of the board sheet K. Thus, as compared with the comparative example in which the whole chip package 208 is mounted on the surface of the circuit board 207 as illustrated in FIG. 12, a larger number of circuit boards 207 can be formed using the board sheet K of the same size, the number of taken circuit boards 207 can be increased, and productivity can be increased.

Examples of the circuit boards include a printed board and a ceramic board.

As illustrated in FIG. 10A, the intake air temperature sensor 203 is disposed so as to protrude from the short side of the circuit board 207 along the longitudinal direction. The through-hole 262 into which the pair of leads 203b of the intake air temperature sensor 203 are inserted is made on the leading edge side of the circuit board 207. In the pair of leads 203b of the intake air temperature sensor 203, each end is inserted into the through-holes 262, bent along the surface of the circuit board 207, and protruded from the short side of the circuit board 207. A solder pad 263 is provided on the circuit board surface of the circuit board 207 opposed to the pair of leads 203b, and the pads 263 and the lead 203b are soldered together. The sensor body 203a is supported at a position separating from the circuit board 207 by a predetermined distance.

As illustrated in FIG. 11A, when the intake air temperature sensor 203 is mounted on each circuit board 207 on the board sheet K, the ends of the pair of leads 203b are inserted into the through-holes 262, and each lead 203b is disposed along the circuit board surface of the circuit board 207. As illustrated in FIGS. 11B and 11C, the sensor body 203a is disposed so as to enter a positioning hole K2 previously made in a frame K1 of the board sheet K. Thus, the intake air temperature sensor 203 is positioned in the correct position with the correct posture with respect to the circuit board 207, soldered in the stably-supported state, and a mounting error with respect to the circuit board 207 can be decreased.

<Configuration of Chip Package 208>

Figure 13A:
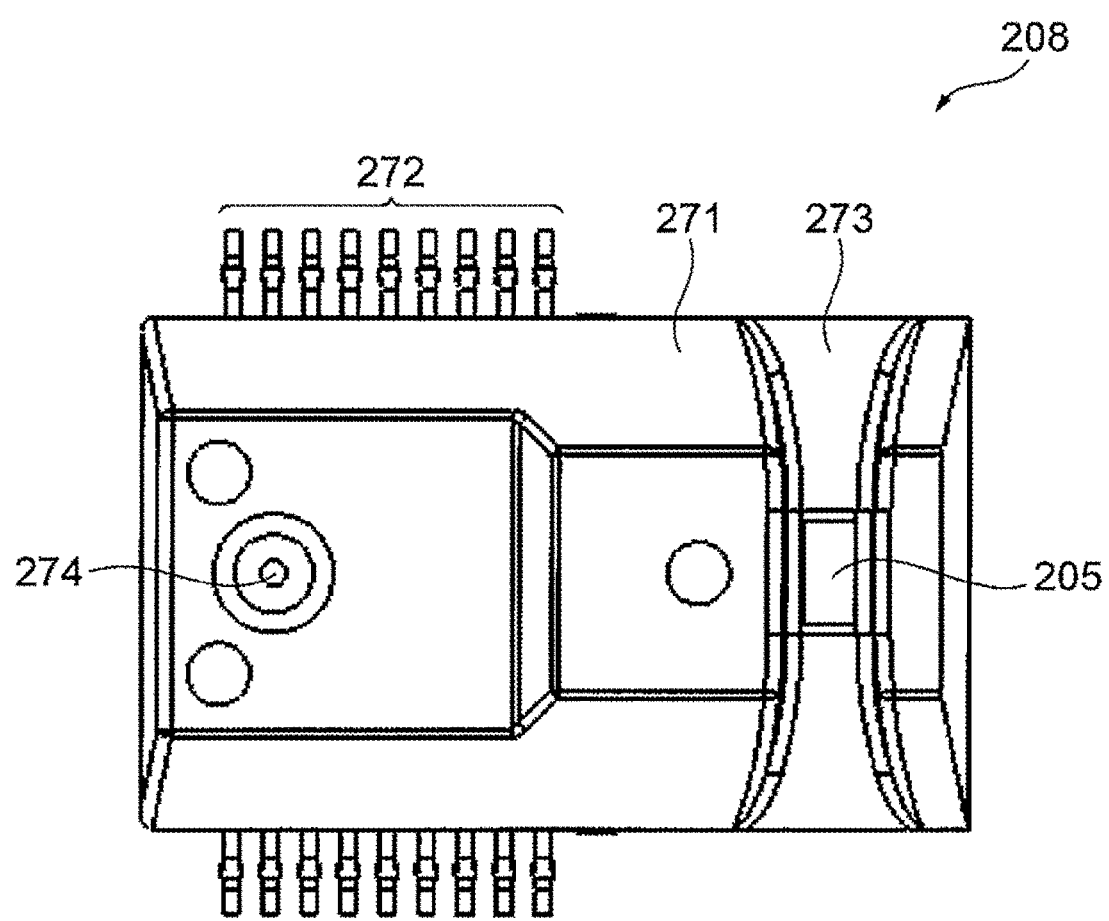
FIG. 13A is a front view of a chip package.
Figure 13B:
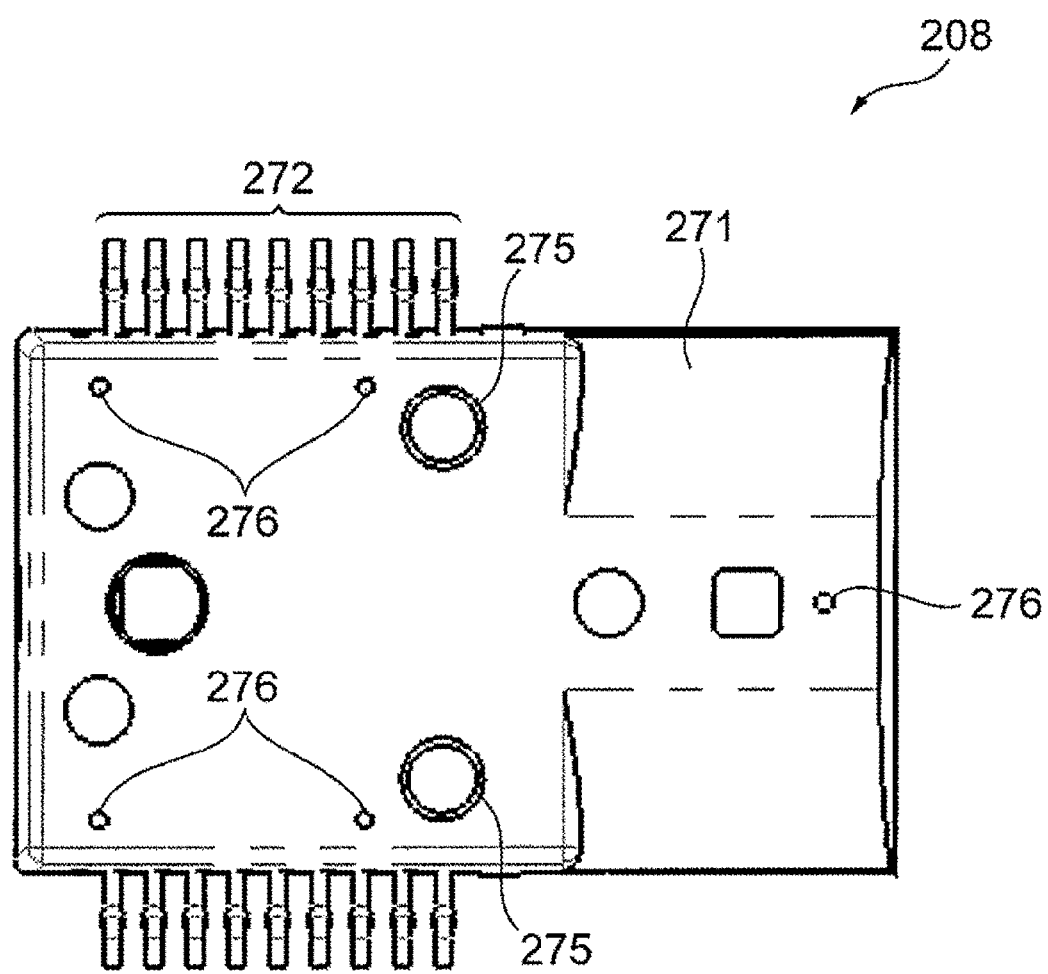
FIG. 13B is a rear view of the chip package.
Figure 13C:
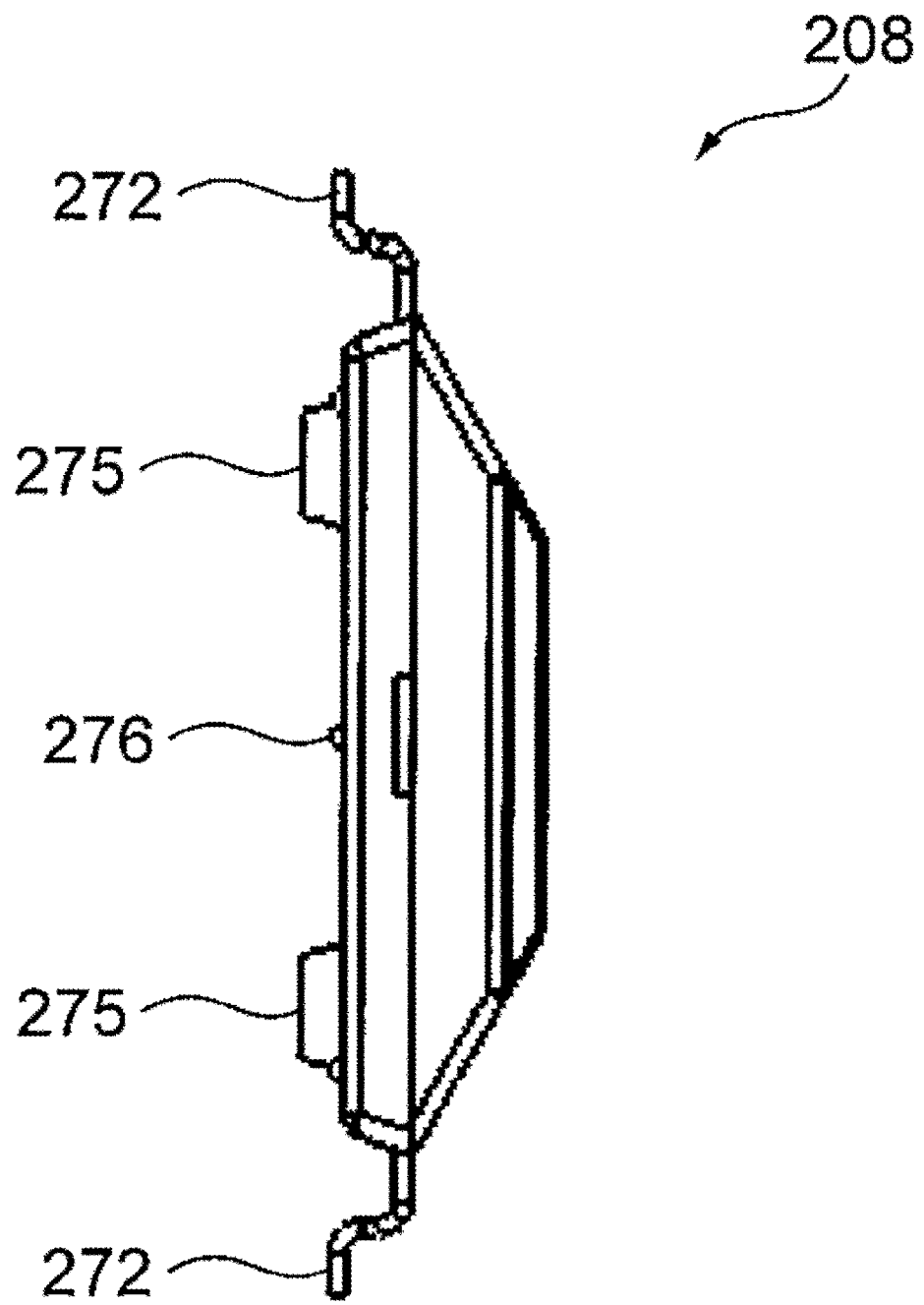
FIG. 13C is a left side view of the chip package.
Figure 13D:
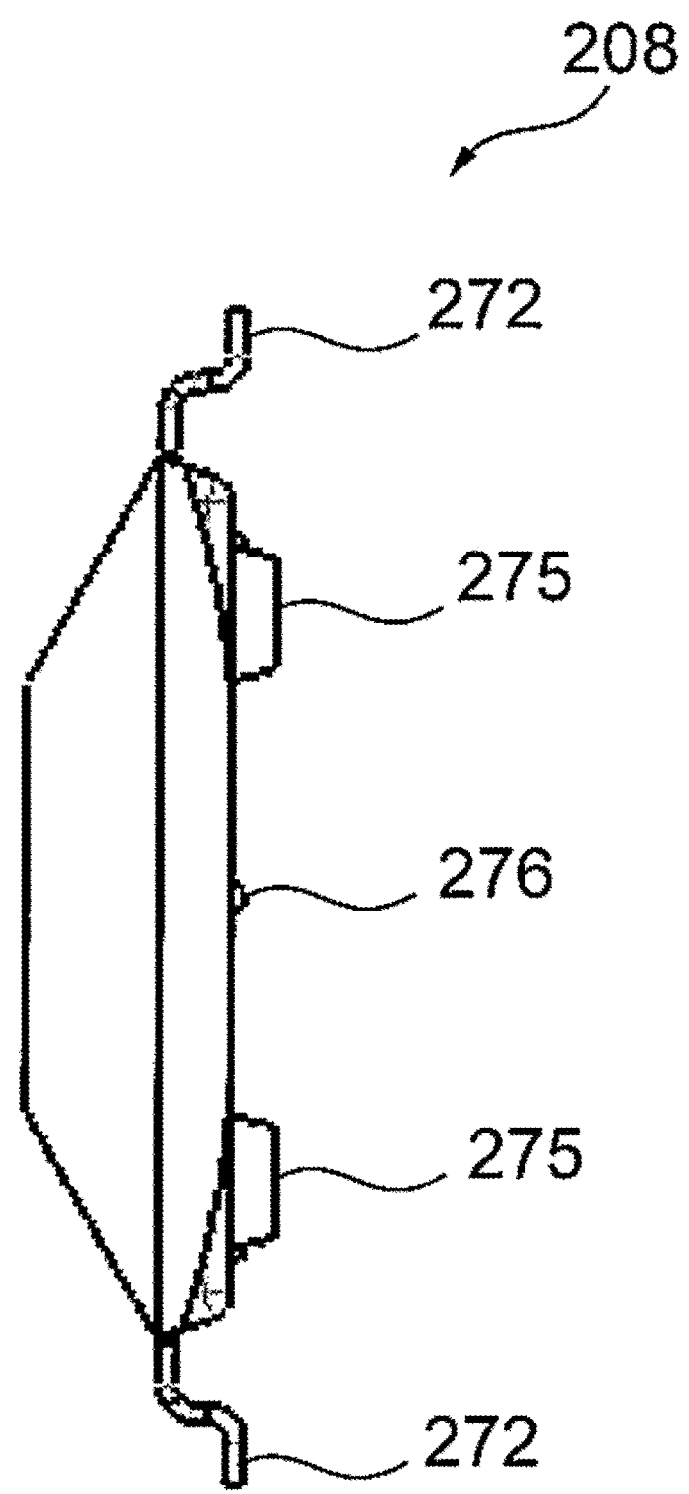
FIG. 13D is a right side view of the chip package.
Figure 13E:
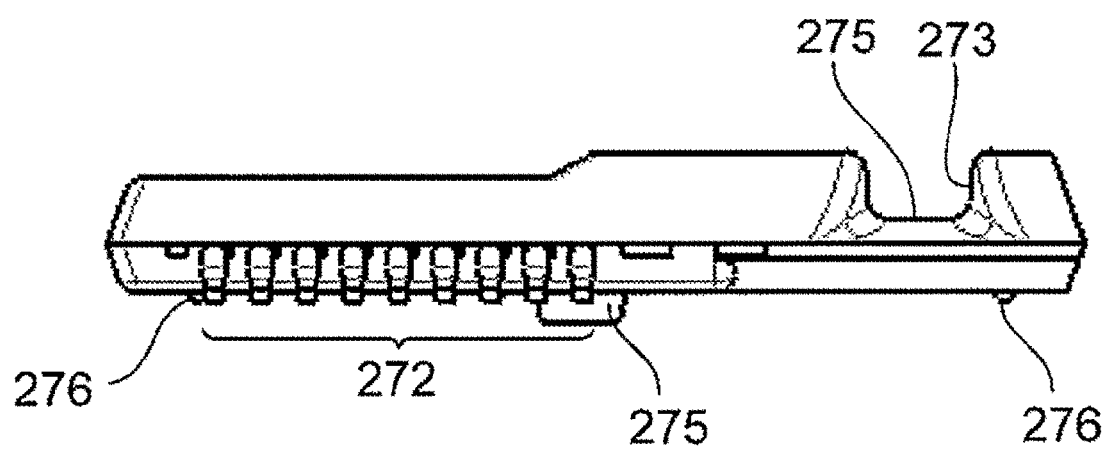
FIG. 13E is a bottom view of the chip package.
Figure 14:
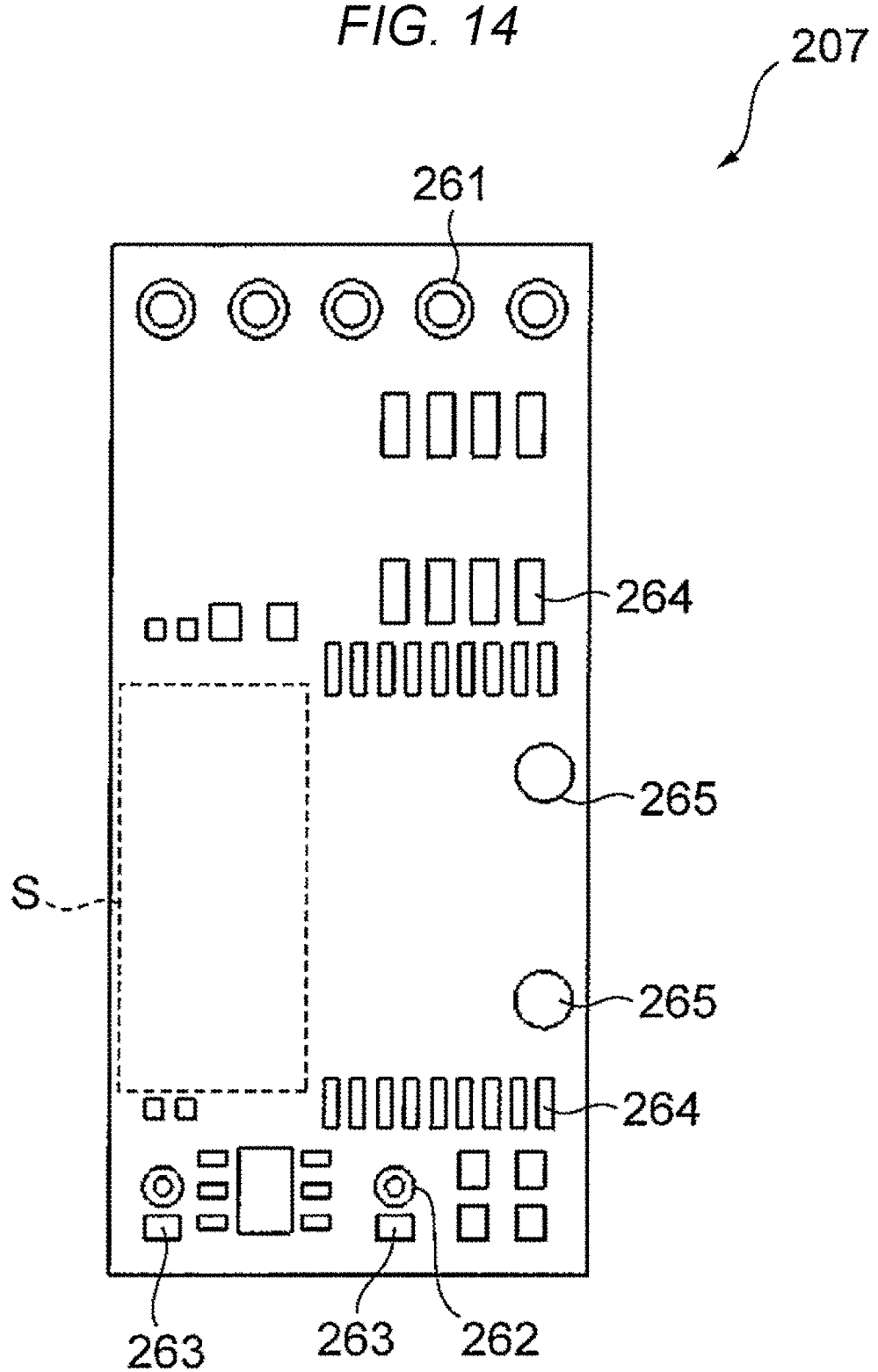
FIG. 14 is a front view illustrating the circuit board on which the circuit component is not mounted.

FIG. 13A is a front view of the chip package, FIG. 13B is a rear view of the chip package, FIG. 13C is a left side view of the chip package, FIG. 13D is a right side view of the chip package, FIG. 13E is a bottom view of the chip package, and FIG. 14 is a front view illustrating the circuit board on which the circuit component is not mounted.

The chip package 208 is configured by mounting the LSI and the flow sensor 205 on a metal lead frame and by sealing the LSI and the flow sensor 205 using a thermosetting resin. The flow sensor 205 and the LSI may integrally be formed by the same semiconductor element, or separately be formed. The chip package 208 includes the package body 271 resin-molded in a substantially flat plate shape. The package body 271 has a rectangular shape and extends along the short-side direction of the measuring unit 213, the base end on one side in the longitudinal direction of the package body 271 is disposed in the circuit chamber 235, and the leading edge side on the other side in the longitudinal direction of the package body 271 is disposed in the second sub-passage groove 252.

A plurality of connection terminals 272 are provided while protruding from the base end side of the package body 271. The chip package 208 is fixed to the circuit board 207 by soldering the plurality of connection terminals 272 to the pad 264 of the circuit board 207.

The flow sensor 205 is provided at the leading edge of the package body 271.

The flow sensor 205 is disposed while exposed in the second sub-passage. The flow sensor 205 is provided in the passage groove 273 recessed in the surface of the package body 271. The passage groove 273 is formed over the whole width from the end on one side in the short-side direction to the other end in the short-side direction along the short-side direction of the package body 271 so as to extend in the second sub-passage groove 252 and along the second sub-passage groove 252.

Preferably, the passage groove 273 is formed such that a place where the flow sensor 205 is mounted is narrowed. This is because the responsiveness can be improved by increasing the flow speed.

The flow sensor 205 has a diaphragm structure, and a closed space chamber is formed on the back face side of the diaphragm of the package body 271. The space chamber is coupled to the ventilation hole 274 open to the surface of the base end of the package body 271 through the ventilation passage formed inside the package body 271.

A positioning protrusion 275 for positioning on the circuit board 207 is provided on the back face of the base end of the package body 271. A pair of positioning protrusions 275 is provided at positions separating from each other in the short-side direction of the package body 271.

A positioning hole 265 into which the positioning protrusion 275 of the package body 271 is inserted is provided in the circuit board 207. The chip package 208 can be positioned with respect to the circuit board 207 by inserting the positioning protrusion 275 of the package body 271 into the positioning hole 265 of the circuit board 207.

A protrusion 276 is provided in the back face of the package body 271 in order to determine the posture of the package body 271 with respect to the circuit board 207 when the chip package 208 is attached to the circuit board 207 of the board sheet K. As illustrated in FIG. 13B, the protrusions are provided at four corners of the base end and the center in the short-side direction of the leading edge.

The protrusion 276 on the base end side abuts on the circuit board surface of the circuit board 207 to support the package body 271 on the circuit board 207, and the protrusion 276 on the leading edge side supports the package body 271 on the margin region S of adjacent another adjacent circuit board 207 as illustrated in FIG. 10A. The protrusion 276 has a hemispherical shape, and can make a point contact with the unevenness or inclination of the circuit board surface of the circuit board 207 to properly support the package body 271.

Because the base end of the package body 271 is disposed on the circuit board 207 while the leading edge of the package body 271 disposed at the position protruding laterally from the circuit board 207, the chip package 208 has a poor balance. For this reason, there is a risk that the leading edge side is lowered onto the back face side of the circuit board 207 while the base end side is inclined so as to be lifted from the surface of the circuit board 207.

In the embodiment, the protrusion 276 is provided on the back face of the package body 271 such that the leading edge and the base end of the package body 271 are supported while placed on both the circuit board 207 and another adjacent circuit board 207, so that the inclination of the package body 271 can be prevented. Thus, the chip package 208 can be fixed to the circuit board 207 in the correct posture by soldering the connection terminal 272 to the pad 264 of the circuit board 207.

Although the embodiment of the present invention have been described in detail above, the present invention is not limited to the above embodiment, but various design changes can be made without departing from the spirit of the present invention described in the claims. For example, the above embodiment has been described in detail for easy understanding of the present invention, and the present invention is not necessarily limited to the embodiment having all the configurations described above. A part of the configuration of an embodiment can be replaced with the configuration of another embodiment, and the configuration of another embodiment can be added to the configuration of an embodiment. Furthermore, another configuration can be added to, deleted from, and replaced with other configurations for a part of the configuration of each embodiment.

REFERENCE SIGNS LIST 1 internal combustion engine control system
2 measured gas
20 physical quantity detection device
22 main passage
201 housing
202 cover
203 intake air temperature sensor
204 pressure sensor
205 flow sensor
206 humidity sensor
207 circuit board
208 chip package
209 hot melt adhesive
211 flange
212 connector
213 measuring unit
214 connector terminal
215 rib (bottom surface of circuit chamber)
221 front face
222 back face
223 side face on one side
224 side face on the other side
226 bottom face on one side
227 bottom face on the other side 228 step surface
231 inlet
232 first outlet
233 second outlet
234 sub-passage
235 circuit chamber
237 rib (bottom surface of circuit chamber)
238 positioning groove
241 fixing hole
242 through-hole
243 first rib
244 second rib
245 third rib
246 fourth rib
247 external terminal
248 correction terminal
250 sub-passage groove
251 first sub-passage groove
252 second sub-passage groove
253 protrusion
261 through-hole (for press fitting)
262 through-hole (for lead)
263 pad (for intake air temperature sensor)
264 pad (for chip package terminal)
265 positioning hole
271 package body
272 connection terminal
273 passage groove
274 ventilation hole
275 positioning protrusion
276 protrusion

The invention claimed is:

1. A physical quantity detection device for measuring physical quantities of a gas comprising intake air in a vehicle, the device comprising:
   a flange used for support in an elongate main passage through which the physical quantities of the gas flow in a flow direction;
   a generally rectangular circuit board on which a plurality of physical quantity sensors are mountable;
   a generally rectangular circuit chamber that accommodates the circuit board; and
   an elongate sub-passage in which a flow sensor is disposed, wherein:
   a lattice-shaped rib is formed on a circuit board mounting portion of the circuit chamber,
   the circuit chamber is located on an upstream side of the sub-passage, and
   the circuit board is disposed with a longitudinal axis of the circuit board in parallel with a longitudinal axis of the circuit chamber, and in parallel with a longitudinal axis of the sub-passage, and in parallel with the direction of flow of the measured gas flowing through the main passage.

2. The physical quantity detection device according to claim 1, wherein the circuit board has a shape in which an aspect ratio is larger than 1, and is mounted in the circuit chamber such that a longitudinal direction of the circuit board is an insertion direction.

3. The physical quantity detection device according to claim 2, further comprising a circuit package that is sealed with resin so as to expose a measuring unit of the flow sensor,
   wherein the circuit package is mounted on the circuit board such that a flow sensor side of the circuit package protrudes from a long side of the circuit board.

4. The physical quantity detection device according to claim 2, wherein the flow sensor is disposed in a protrusion protruding from a long side of the circuit board to a sub-passage.

5. The physical quantity detection device according to claim 2, wherein the flow sensor is disposed in the circuit board with a support that is a separate member being interposed between the flow sensor and the circuit board, and the support is provided so as to protrude from a long side of the circuit board to the sub-passage.

6. The physical quantity detection device according to claim 3, wherein the circuit package has a narrowed portion in a place exposed to the sub-passage on a surface on the flow sensor side.

7. The physical quantity detection device according to claim 6, wherein the circuit board includes a pressure sensor mounting portion, a flow sensor mounting portion, a humidity sensor mounting portion, and an intake air temperature sensor mounting portion in order closest to the flange.

8. The physical quantity detection device according to claim 6, wherein in the circuit board, a pressure sensor, the flow sensor, a humidity sensor, and a temperature sensor are provided in order closest to the flange.

9. The physical quantity detection device according to claim 7 wherein an inlet opening of the sub-passage is formed on a downstream side of an upstream sidewall of the circuit chamber.

10. The physical quantity detection device according to claim 9, wherein an intake air temperature sensor is disposed at the downstream side of the upstream sidewall and on an upstream side of the inlet opening of the sub-passage.

11. The physical quantity detection device according to claim 10, further comprising a protector for the intake air temperature sensor,
   wherein the intake air temperature sensor is disposed on an inlet opening projection surface of the sub-passage.

* * * * *